US012402807B2

(12) United States Patent
Thomas et al.

(10) Patent No.: US 12,402,807 B2
(45) Date of Patent: Sep. 2, 2025

(54) PATIENT MONITORING SYSTEM AND METHOD

(71) Applicant: TIDI Products, LLC, Neenah, WI (US)

(72) Inventors: Justin K. Thomas, Niles, IL (US); Samantha L. McCarthy, Libertyville, IL (US); Eduardo Villagran Hernandez, Tijuana (MX); Brian Nathan Young, Lombard, IL (US); Melissa Waldroup, Round Lake, IL (US); Joseph Samz, Appleton, WI (US)

(73) Assignee: TIDI Products, LLC, Neenah, WI (US)

( * ) Notice: Subject to any disclaimer, the term of this patent is extended or adjusted under 35 U.S.C. 154(b) by 0 days.

(21) Appl. No.: 18/388,701

(22) Filed: Nov. 10, 2023

(65) Prior Publication Data
US 2024/0074677 A1    Mar. 7, 2024

Related U.S. Application Data

(63) Continuation of application No. PCT/US2022/028815, filed on May 11, 2022.
(Continued)

(51) Int. Cl.
*A61B 5/11* (2006.01)
*A61B 5/00* (2006.01)

(52) U.S. Cl.
CPC .......... *A61B 5/1117* (2013.01); *A61B 5/0026* (2013.01); *A61B 2560/0204* (2013.01);
(Continued)

(58) Field of Classification Search
CPC ................ A61B 5/1117; A61B 5/0026; A61B 2560/0204; A61B 2560/0406;
(Continued)

(56) References Cited

U.S. PATENT DOCUMENTS

| 558,641 | A | 4/1896 | Ensign |
| 3,182,338 | A | 5/1965 | Shirrod |

(Continued)

FOREIGN PATENT DOCUMENTS

| CN | 102087774 B | 6/2011 |
| CN | 203204788 U | 9/2013 |

(Continued)

OTHER PUBLICATIONS

"Search Report for PCT Patent Application No. PCT/US22/28815 "Patient Monitoring System and Method" dated Sep. 21, 2022, 5 pages filed herewith" (Year: 2022).*

(Continued)

*Primary Examiner* — Omar Casillashernandez
(74) *Attorney, Agent, or Firm* — Amundsen Davis, LLC

(57) ABSTRACT

A monitoring apparatus and method includes a monitor, a sensor comprising a wireless connection with the monitor, and an adapter comprising the wireless connection with the monitor and a wired or wireless connection with a remote monitoring station. The monitor is designed to wirelessly pair with the sensor and/or the adapter when being only positioned by a user in a closed proximity to the sensor and/or the adapter or in a direct contact with the sensor and/or the adapter and without an additional action by the user and/or a wired connection between the monitor and the sensor and/or the adapter. A pairing alignment mark may be provided on each of the monitor, sensor and adapter.

31 Claims, 14 Drawing Sheets

Related U.S. Application Data

(60) Provisional application No. 63/187,169, filed on May 11, 2021.

(52) U.S. Cl.
CPC ............... *A61B 2560/0406* (2013.01); *A61B 2562/0247* (2013.01)

(58) Field of Classification Search
CPC .. A61B 2562/0247; A61B 5/002; G08B 7/06; G08B 21/043
USPC ........................................................ 600/595
See application file for complete search history.

(56) References Cited

U.S. PATENT DOCUMENTS

| | | | |
|---|---|---|---|
| 4,132,229 A | 1/1979 | Morrison | |
| 4,226,007 A | 10/1980 | Duenser | |
| 4,417,572 A | 11/1983 | Green | |
| 4,608,973 A | 9/1986 | Green et al. | |
| 4,777,944 A | 10/1988 | Green et al. | |
| 4,907,845 A | 3/1990 | Wood | |
| 4,967,195 A * | 10/1990 | Shipley | G08B 26/001 340/286.07 |
| 5,076,288 A | 12/1991 | Millard et al. | |
| 5,161,545 A | 11/1992 | McCarthy | |
| 5,492,285 A | 2/1996 | Hamrick | |
| 5,494,046 A | 2/1996 | Cross | |
| 5,554,835 A | 9/1996 | Newham | |
| 5,585,789 A | 12/1996 | Haneda | |
| 5,627,520 A | 5/1997 | Grubbs et al. | |
| 5,651,376 A | 7/1997 | Thompson | |
| 5,654,694 A | 8/1997 | Newham | |
| 5,751,214 A | 5/1998 | Cowley et al. | |
| 5,785,011 A | 7/1998 | Gitterman, III | |
| 5,844,488 A | 12/1998 | Musick | |
| D404,845 S | 1/1999 | McIntyre et al. | |
| 6,078,261 A | 6/2000 | Davsko | |
| 6,111,509 A | 8/2000 | Holmes | |
| 6,119,314 A | 9/2000 | Freed | |
| 6,166,644 A | 12/2000 | Stroda | |
| 6,239,704 B1 | 5/2001 | Olson | |
| 6,311,374 B1 | 11/2001 | Anscher | |
| 6,441,742 B1 | 8/2002 | Lovely et al. | |
| 6,544,200 B1 | 4/2003 | Smith et al. | |
| 6,557,557 B2 | 5/2003 | Hamama | |
| 6,561,987 B2 | 5/2003 | Pail | |
| 6,727,445 B2 | 4/2004 | Cullinan et al. | |
| 6,778,090 B2 | 8/2004 | Newham | |
| 6,784,797 B2 | 8/2004 | Smith et al. | |
| 6,796,007 B1 | 9/2004 | Anscher | |
| 6,847,301 B1 | 1/2005 | Olson | |
| 6,897,781 B2 | 5/2005 | Cooper et al. | |
| 6,917,293 B2 | 7/2005 | Beggs | |
| 6,987,232 B2 | 1/2006 | Smith et al. | |
| 6,998,986 B2 | 2/2006 | Smith | |
| 7,078,676 B2 | 7/2006 | Smith et al. | |
| 7,079,036 B2 | 7/2006 | Cooper et al. | |
| 7,253,366 B2 | 8/2007 | Bhai | |
| 7,282,031 B2 | 10/2007 | Hendrich | |
| 7,319,400 B2 | 1/2008 | Smith et al. | |
| 7,378,975 B1 | 5/2008 | Smith et al. | |
| 7,412,899 B2 | 8/2008 | Mian et al. | |
| 7,420,472 B2 | 9/2008 | Tran | |
| 7,557,719 B1 | 7/2009 | Long | |
| 7,568,246 B2 | 8/2009 | Weismiller et al. | |
| 7,570,152 B2 | 8/2009 | Smith et al. | |
| 7,656,299 B2 | 2/2010 | Gentry et al. | |
| 7,666,151 B2 | 2/2010 | Sullivan et al. | |
| 7,682,308 B2 | 3/2010 | Hendrich | |
| 7,746,218 B2 | 6/2010 | Collins, Jr. et al. | |
| 7,768,949 B2 | 8/2010 | Perkins et al. | |
| 7,836,529 B2 | 11/2010 | Cherubini et al. | |
| 7,883,480 B2 | 2/2011 | Dunlop | |
| 7,916,036 B1 | 3/2011 | Pope et al. | |
| 7,924,163 B1 | 4/2011 | Long et al. | |
| 7,938,121 B2 | 5/2011 | McKnight et al. | |
| 8,085,154 B2 | 12/2011 | Williams et al. | |
| 8,203,454 B2 | 6/2012 | Knight et al. | |
| 8,211,014 B2 | 7/2012 | David et al. | |
| 8,325,053 B2 | 12/2012 | Flynt et al. | |
| D680,900 S | 4/2013 | Grimm | |
| 8,416,084 B2 | 4/2013 | Beltmann et al. | |
| 8,449,471 B2 | 5/2013 | Tran | |
| 8,451,129 B2 | 5/2013 | Hamdan | |
| 8,477,039 B2 | 7/2013 | Gleckler et al. | |
| 8,500,636 B2 | 8/2013 | Tran | |
| 8,521,490 B2 | 8/2013 | Hardigan | |
| 8,529,448 B2 | 9/2013 | McNair | |
| 8,604,917 B2 | 12/2013 | Collins et al. | |
| D701,139 S | 3/2014 | Kadoishi | |
| 8,708,903 B2 | 4/2014 | Tran | |
| 8,717,181 B2 | 5/2014 | Tallent et al. | |
| 8,749,391 B2 | 6/2014 | Flinsenberg et al. | |
| 8,752,220 B2 | 6/2014 | Soderberg et al. | |
| 8,866,620 B2 | 10/2014 | Amir | |
| D717,206 S | 11/2014 | Iannello et al. | |
| 8,886,334 B2 | 11/2014 | Ghaffari et al. | |
| 8,911,377 B2 | 12/2014 | Al-Ali | |
| 8,933,801 B2 | 1/2015 | Sweeney et al. | |
| 8,968,195 B2 | 3/2015 | Tran | |
| 8,990,041 B2 | 3/2015 | Grabiner et al. | |
| 9,013,313 B2 | 4/2015 | Paine | |
| 9,064,482 B2 | 6/2015 | Henriques | |
| 9,098,993 B2 | 8/2015 | Reed, Jr. | |
| 9,153,114 B2 | 10/2015 | Yi et al. | |
| 9,165,449 B2 | 10/2015 | Ribble et al. | |
| 9,202,361 B2 | 12/2015 | Andres et al. | |
| D749,462 S | 2/2016 | Pail et al. | |
| 9,275,533 B2 | 3/2016 | Sullivan et al. | |
| 9,311,540 B2 | 4/2016 | Ecker et al. | |
| 9,314,159 B2 | 4/2016 | Lyon et al. | |
| 9,386,863 B1 | 7/2016 | Antunovic | |
| 9,411,934 B2 | 8/2016 | Robinson et al. | |
| 9,466,204 B2 | 10/2016 | Olson | |
| 9,468,399 B2 | 10/2016 | Shinozuka et al. | |
| 9,480,307 B2 | 11/2016 | Makley | |
| 9,495,855 B2 | 11/2016 | Hanson et al. | |
| 9,558,641 B2 | 1/2017 | Brasch et al. | |
| D778,779 S | 2/2017 | Fujii | |
| 9,705,321 B1 | 7/2017 | Frink et al. | |
| 9,770,144 B2 | 9/2017 | Rife et al. | |
| 9,795,321 B2 | 10/2017 | Shimzu | |
| 9,808,194 B2 | 11/2017 | Bhat et al. | |
| 9,814,637 B2 | 11/2017 | Sazonov | |
| 9,861,321 B2 | 1/2018 | Collins, Jr. et al. | |
| 9,866,797 B2 | 1/2018 | Clark et al. | |
| 9,940,807 B1 | 4/2018 | Brasch et al. | |
| 9,940,810 B2 | 4/2018 | Derenne et al. | |
| 10,020,075 B2 | 7/2018 | Perlman et al. | |
| 10,043,368 B1 | 8/2018 | Fonzi, III et al. | |
| 10,098,593 B2 | 10/2018 | Collins, Jr. et al. | |
| 10,188,296 B2 | 1/2019 | Al-Ali et al. | |
| 10,292,661 B1 | 5/2019 | Laborde | |
| 10,357,197 B2 | 7/2019 | Smith et al. | |
| 10,383,527 B2 * | 8/2019 | Al-Ali | A61B 5/743 |
| 10,438,475 B2 | 10/2019 | Williams | |
| 10,438,496 B2 | 10/2019 | Panzer | |
| 10,470,685 B2 | 11/2019 | Son et al. | |
| 10,470,689 B2 | 11/2019 | Kilcran et al. | |
| 10,517,511 B2 | 12/2019 | Charna | |
| 10,593,185 B2 | 3/2020 | Brasch et al. | |
| 10,646,171 B2 | 5/2020 | Brasch et al. | |
| 10,674,940 B2 | 6/2020 | Kilcran et al. | |
| 10,722,146 B2 | 7/2020 | Kilcran et al. | |
| 10,799,153 B2 | 10/2020 | Kilcran et al. | |
| 10,806,377 B2 | 10/2020 | Kilcran et al. | |
| 11,020,046 B2 | 6/2021 | Lee et al. | |
| 11,083,418 B2 | 8/2021 | Ferber | |
| 11,141,030 B2 | 10/2021 | Newham | |
| 11,210,922 B2 | 12/2021 | Carr et al. | |
| 12,150,754 B2 | 11/2024 | Kilcran et al. | |
| 2002/0068883 A1 | 6/2002 | Hamama | |

(56) References Cited

U.S. PATENT DOCUMENTS

| | | |
|---|---|---|
| 2003/0197614 A1 | 10/2003 | Smith et al. |
| 2004/0111045 A1 | 6/2004 | Sullivan et al. |
| 2005/0076920 A1 | 4/2005 | Dubats |
| 2005/0080360 A1 | 4/2005 | Katz et al. |
| 2005/0150503 A1 | 7/2005 | Votel |
| 2007/0040692 A1 | 2/2007 | Smith et al. |
| 2008/0169931 A1 | 7/2008 | Gentry et al. |
| 2008/0205311 A1 | 8/2008 | Perkins et al. |
| 2010/0109879 A1 | 5/2010 | Hamdan |
| 2010/0298742 A1 | 11/2010 | Perlman et al. |
| 2011/0034845 A1 | 2/2011 | Polliack et al. |
| 2011/0133935 A1 | 6/2011 | Beltmann et al. |
| 2011/0152632 A1* | 6/2011 | Le Neel ............... A61B 5/0024 600/300 |
| 2012/0032808 A1 | 2/2012 | Cherubini |
| 2012/0095722 A1 | 4/2012 | Kate |
| 2012/0154155 A1 | 6/2012 | Brasch |
| 2013/0019882 A1 | 1/2013 | Durham et al. |
| 2013/0178893 A1 | 7/2013 | Hathom |
| 2014/0039351 A1 | 2/2014 | Mix et al. |
| 2014/0145848 A1 | 5/2014 | Amir |
| 2014/0221876 A1 | 8/2014 | Eddy |
| 2014/0224262 A1 | 8/2014 | Parent et al. |
| 2014/0232556 A1 | 8/2014 | Williams |
| 2015/0039794 A1 | 2/2015 | Williams |
| 2015/0157488 A1 | 6/2015 | Grunden et al. |
| 2015/0226764 A1 | 8/2015 | Kate |
| 2015/0257685 A1 | 9/2015 | Pushpala et al. |
| 2015/0351690 A1 | 12/2015 | Toth et al. |
| 2016/0082217 A1 | 3/2016 | McLaren et al. |
| 2016/0196733 A1 | 7/2016 | Brasch et al. |
| 2016/0198809 A1 | 7/2016 | Grunden et al. |
| 2016/0307429 A1 | 10/2016 | Hood et al. |
| 2017/0124844 A1 | 5/2017 | Huster et al. |
| 2017/0172473 A1* | 6/2017 | Wedekind ............... A61B 5/002 |
| 2017/0236398 A1 | 8/2017 | Eddy et al. |
| 2017/0362004 A1 | 12/2017 | Prevot et al. |
| 2018/0125413 A1 | 5/2018 | Smith et al. |
| 2018/0168459 A1 | 6/2018 | Tran |
| 2018/0174679 A1 | 6/2018 | Sampath et al. |
| 2018/0206794 A1 | 7/2018 | Laborde |
| 2018/0228386 A1 | 8/2018 | McCall et al. |
| 2018/0303383 A1 | 10/2018 | Connor |
| 2019/0038183 A1 | 2/2019 | Carr |
| 2019/0046084 A1 | 2/2019 | Kilcran et al. |
| 2019/0110761 A1 | 4/2019 | Brasch et al. |
| 2019/0297966 A1* | 10/2019 | Wisniewski .......... A61F 13/128 |
| 2019/0304283 A1 | 10/2019 | Carr et al. |
| 2020/0020240 A1 | 1/2020 | Panzer |
| 2020/0077892 A1 | 3/2020 | Tran |
| 2020/0113487 A1 | 4/2020 | Charna |
| 2020/0306528 A1* | 10/2020 | Linden ............... A61N 1/36114 |
| 2020/0320843 A1 | 10/2020 | Carr et al. |
| 2021/0084700 A1 | 3/2021 | Daniels |
| 2022/0054047 A1 | 2/2022 | Kilcran et al. |
| 2024/0130634 A1 | 4/2024 | Kilcran et al. |

FOREIGN PATENT DOCUMENTS

| | | |
|---|---|---|
| CN | 105361347 A | 3/2016 |
| CN | 205729594 U | 11/2016 |
| CN | 208049218 U | 11/2018 |
| CN | 109310167 B | 2/2019 |
| CN | 106999300 B | 2/2020 |
| EP | 0985375 A2 | 3/2000 |
| EP | 2384726 A1 | 11/2011 |
| KR | 101585364 B1 | 1/2016 |
| TW | M542454 U | 6/2017 |
| WO | 2020257475 A1 | 12/2020 |

OTHER PUBLICATIONS

AliMed Roll Control Belt With Alarm, Website, retrieved from the internet at least as early as Jun. 17, 2019; 1 page; https://www.alimed.com/alimed-roll-control-belt-with-alarm.html.

DeRoyal Double-Lock Security Cuffs, Leather Limb Holders, and Fixed Position Cuffs, retrieved at least as early as Nov. 18, 2017; 10 pages.

E.M. Adams Company Limb Holder Application Instruction, retrieved at least as early as Nov. 16, 2017; 5 pages.

E-Z Release Seat Belts w/Alarm by Alimed, retrieved from the internet at least as early as Jul. 10, 2017; Website, 1 page; www.medline.com.

International Search Report for PCT/US2018/045121, "Predictive Double-Release Alarm Belt" dated Oct. 22, 2018; 2 pages.

MDT5500 Patient Alarm Belt Replacement, retrieved from the internet at least as early as Jul. 10, 2017, Website, 1 page, www.medline.com.

Parasol Wireless Fall Prevention System Instructional Video, YouTube video, May 23, 2017, Parasol Medical, https://youtube/6zNgyqHUcao, 135 pages.

Posey Healthcare Products Guide 1996; 2 pages.

Posey Patient Safety Aids—1985 Edition—Product Catalog; 6 pages.

Posey Patient Safety Aids—1989-1990 Product Line; 4 pages.

Posey Self-Releasing Chair Belt Sensors, retrieved at least as early as Jun. 17, 2019, Instruction sheet; 2 pages, Posey Company.

Search Report for PCT Patent Application No. PCT/US2020/038080, "Integrated Belt Sensor for Alarm for Patient Furniture" dated Sep. 3, 2020, 3 pages.

Smart Caregiver TL-2109 Early Warning Chair Belts, retrieved from the internet at least as early as Jul. 10, 2017, Website, 1 page, www.quickmedical.com.

Alimed, "IQ Cordless Sensor Alarm", available on the internet on or before Oct. 21, 2018 at https://www.alimed.com/alimed-iq-cordless-sensor-alarm.html, 2 pages.

Alimed, "Patient Alarm/Transmitter Unit", available on the internet on or before Oct. 21, 2018 at https://www.alimed.com/replacement-patient-alarm-transmitter-unit.html?pid=155769, 2 pages.

Alimed, "Remote Receiver Alarm Unit", available on the internet on or before Oct. 21, 2018 at https://www.alimed.com/remote-receiver-alarm-unit.html, 2 pages.

Indigo Care, "Wireless Fall Prevention", available on the internet on or before Oct. 21, 2018 at http://www.indigocare.com.au/pages/fall_prevention_products_wireless.html, 2 pages.

Medguard, "Ramblegard Wireless Systems", retrieved from the internet on or before Oct. 21, 2018 at https://www.medguard.ie/ramblegard-wireless-bedgard-chair-pad-with-wireless-jack.html, 5 pages.

S&E CareTrade, "Medical Fall Prevention Equipment Wireless", available on the internet on or before Oct. 21, 2018 at https://www.secaretrade.com/category/MedicalFallPreventionEquipmentWireless, 4 pages.

Smart Caregiver, "Wireless Fall Prevention", available on the internet on or before Oct. 21, 2018 at https://web.archive.org/web/20170224222108/http://smartcaregiver.com/wireless-call-system-with-caregiver-paging, 2 pages.

Unified Alerts, "How do silent bed and chair sensors work" YouTube video, available on the internet on or before Oct. 21, 2018 at https://www.youtube.com/watch?v=Ps8YRhcfS70, 68 pages.

Office Action and Search Report for 202080057957.3, "Integrated Belt and Sensor for Alarm for Patient Furniture" dated Aug. 10, 2023, 14 pages (including Google translations).

Stanley Healthcare, "Fall Management System M200 Fall Monitor", manual, 2016, Stanley Security Solutions, Lincoln, Nebraska, 44 pages filed herewith.

Posey, "Sitter Elite Instruction Manual", manual 2015, Posey Company, Arcadia, California, 40 pages filed herewith.

Office Action for China Patent Application No. 201910998016.9, "Electronic Fall Monitoring System" dated Jul. 5, 2022, 14 pages filed herewith.

Extended European Search Report for EP 22808283.0, dated Jan. 15, 2025, 11 pages.

* cited by examiner

PATIENT MONITORING SYSTEM AND METHOD

CROSS-REFERENCE TO RELATED APPLICATIONS

This application is a continuation of PCT Application No. PCT/US22/28815, filed May 11, 2022, which claims the benefit of U.S. Provisional Application No. 63/187,169, filed May 11, 2021, and titled: PATIENT MONITORING SYSTEM AND METHOD.

TECHNICAL FIELD

The subject matter relates to a field of patient care. It further relates to an electronic patient monitoring with a monitor wirelessly connecting to a patient sensor for detecting activations indicating physical presence of a patient at the patient sensor and deactivations indicating loss of physical presence of the patient at the patient sensor.

BACKGROUND

Patient monitoring systems are typically used in healthcare and care facilities to provide an early warning as to when a patient who is at risk for falling is attempting to get up without assistance. Although patient monitoring systems do not themselves prevent falls, they can provide advance notification to others that a patient is or may be moving from the sensor so that assistance can be rendered.

Patient monitoring systems typically include a device connected to a pressure sensitive sensor or mat. When a patient rests on the sensor, which could be placed on a bed, a chair or a toilet, the sensor triggers the device to begin monitoring. When the patient later moves from the sensor, unless the device is suspended or powered down, the device can initiate an alarm. Possible alarms include an indicator light, an audible tone, playback of a recorded statement to return to the sensor and/or a message sent to a nurse call station. While patient monitoring systems are effective for providing early warning when a patient is moving, it is nevertheless desirable to at least increase ease of use where possible.

BRIEF DESCRIPTION OF THE DRAWINGS

The accompanying drawings are incorporated in and constitute part of the specification and illustrate various embodiments. In the drawings.

DETAILED DESCRIPTION OF THE DISCLOSURE

Figure 1:
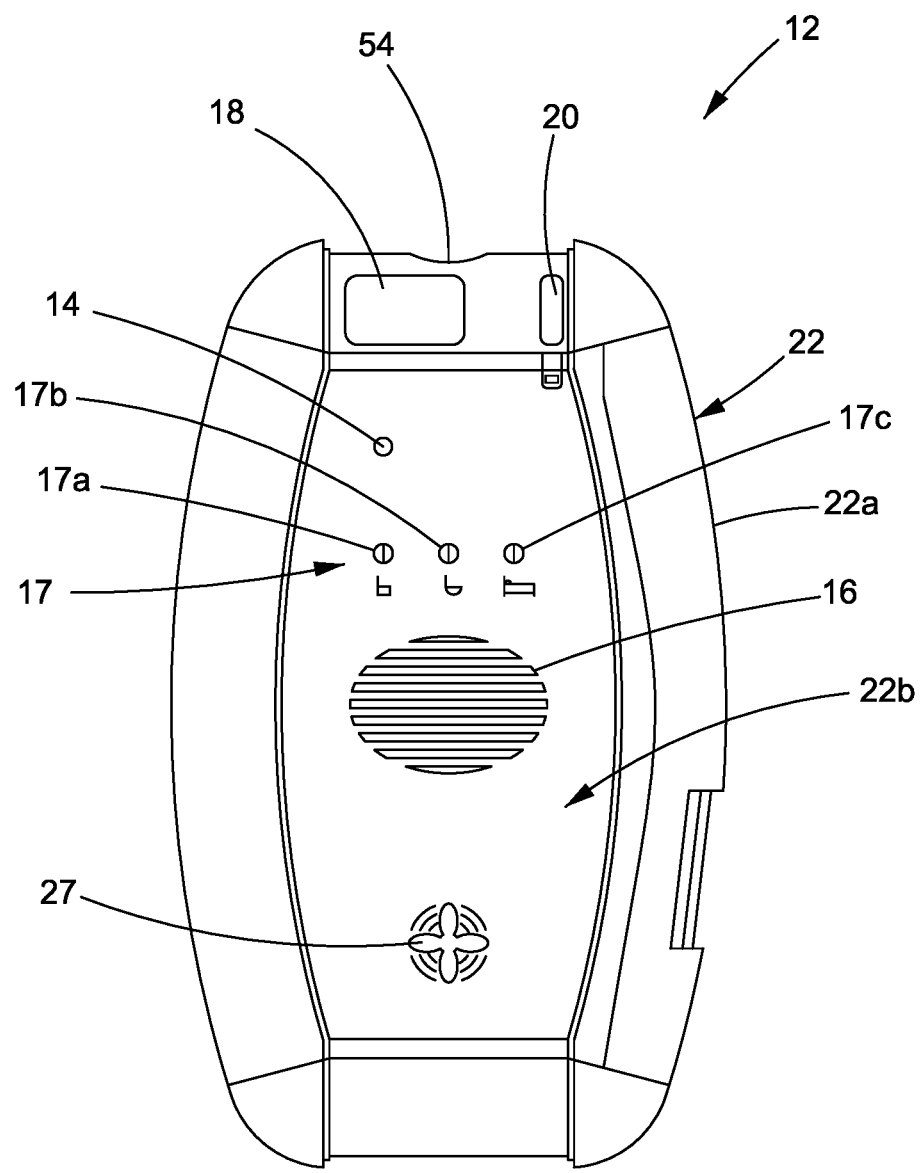
FIG. 1 illustrates a front view of a monitor.

Prior to proceeding to the more detailed description of the present disclosure, it should be noted that, for the sake of clarity and understanding, identical components which have identical functions have been identified with identical reference numerals throughout the several views illustrated in the drawing figures.

The terms and words used in the following description and claims are not limited to the bibliographical meanings, but, are merely used to enable a clear and consistent understanding of the exemplary embodiments. Accordingly, it should be apparent to those skilled in the art that the following description of exemplary embodiments are provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

For purposes here, the conjunction "or" is to be construed inclusively (e.g., "a dog or a cat" would be interpreted as "a dog, or a cat, or both"; e.g., "a dog, a cat, or a mouse" would be interpreted as "a dog, or a cat, or a mouse, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes here, the words "comprising," "including," "having," and variants thereof, wherever they appear, shall be construed as open-ended terminology, with the same meaning as if the phrase "at least" were appended after each instance thereof.

The verb "may" is used to designate optionality/noncompulsoriness. In other words, something that "may" can, but need not.

Before elucidating the subject matter shown in the Figures, the present disclosure will be first described in general terms. As used herein, the term "sensor-adapter" is defined to mean a unit that can function as one or both of a "sensor" and an "adapter", as these individual terms are used and defined herein and understood by one of ordinary skill in the art.

The present disclosure provides a monitor that is designed to monitor a sensor connected to the monitor and communicate an operating condition of the sensor to a remote location, either directly or through an adapter.

The monitor may be designed as a housing with a controller, a connection to the sensor and a user interface that is electrically connected to the controller and may be connected to the sensor.

The housing may be also referred to as a monitor housing. The housing includes a peripheral wall. The peripheral wall defines a hollow interior of the housing. The peripheral wall may be provided as a one-piece member or may be designed as an assembly of two or more portions. The housing may also be referred to as an enclosure. The housing may also be referred to as a casing. The housing may also be referred to as a hollow enclosure and/or as a hollow casing. A back portion of the housing may include a recess for mounting the monitor to a support mechanism. The support mechanism could be, for example, a bracket, clip, bar or other arrangement held to a structure, such as a wall or chair.

The controller may be referred to in this document as a monitor controller. The controller is mounted within the hollow interior. The controller may be provided as a single electronic component or as an assembly of electronic components to connect to and communicate with the sensor to be monitored, monitor any one of a condition, operation and a status of the sensor and perform various operations related to monitoring, including responses to user actions. The controller may be designed with a monitoring circuit or module and a transmission circuit or module. The controller may be constructed of any electrical component, or group of electrical components, that are capable of carrying out the functions described herein. The controller may be designed as a microcontroller. The controller may include one or more micro-processors and a memory that is not a transitory propagating signal. The memory is connected to the one or more processors and encodes readable instructions, including processor executable program instructions, the readable instructions accessible to the one or more processors, wherein the processor executable program instructions, when executed by the one or more processors, cause the one or more processors to perform operations. The instructions followed by the controller in carrying out the functions described herein, as well as the data necessary for carrying out these functions, are stored in a memory accessible by the one or more micro-processors. Readable instructions may be referred to as machine instructions. The controller may include any one or more microcontrollers, field programmable gate arrays, systems on a chip, volatile or nonvolatile memory, discrete circuitry, and/or other hardware, software, or firmware that is capable of carrying out the functions described herein. Such components may be physically configured in any suitable manner, such as by mounting them to one or more circuit boards, or arranging them in other manners, whether combined into a single unit (module) or distributed across multiple units (modules).

The connection to the sensor may be a wired connection. The wire connection includes a cable connecting the sensor with a sensor port within the monitor. The sensor port may be provided as a registered jack port of any applicable standard. The sensor port may be provided as RJ11 port. The sensor port may be provided as RJ 12 port. The sensor port may be provided as a two-port modular jack. Signal from each port may be treated by the monitor controller as a discrete input. The sensor port may be provided as a component of the user interface.

The connection to the sensor may be a wireless connection, using any wireless communication mode or protocol. The wireless connection may be designed as an RFID tag within the sensor and an RFID reader within the controller. The wireless connection may be designed as a Bluetooth® wireless communication protocol or standard. The wireless connection may be designed as a near field or short-range communication (NFC). The NFC wireless communication may include an NFC tag in the sensor and an NFC reader in the monitor. The NFC reader may connect to NFC coil through wire leads. In a wireless communication mode, the monitor can pair up with the sensor in a first wireless connection, which may be an NFC, and exchange communication with the monitor in a second wireless connection, which may be a short range wireless communication, for example such as Bluetooth® standard. When NFC standard is used to pair the monitor with the sensor, a short-range communication is enabled between the monitor and the sensor being adjacent or in a close proximity to each other. With the NFC standard, the monitor is designed to wirelessly pair with the sensor when being only positioned by a user in a close proximity to the sensor or in a direct contact with the sensor and without an additional action by the user and/or a wired connection between the monitor and the sensor. A Bluetooth® Low Energy (BLE) standard may be used for low power consumption. Either wireless connection includes an antenna. The antenna may be electrically connected to the controller. The antenna may be printed, as a trace, on a circuit board of the controller. BLE module may include integrated antenna. When the monitor communicates by way of NFC and Bluetooth®, the monitor may be designed with two antennas, an NFC antenna and a Bluetooth® antenna. The monitor may be also designed to indicate a location of the antenna within the housing for ease of pairing with the monitor in a wireless communication. Such pairing alignment mark would be positioned on the exterior surface of the housing adjacent an antenna location. During use, the pairing alignment mark on the monitor housing is generally aligned with a complimentary pairing alignment mark on the sensor. The alignment of the pairing alignment marks does not have to be precise. In other words, it is not necessary to position one pairing alignment mark exactly at the other pairing alignment mark. The user has to position the monitor either in a close proximity to the sensor and/or adapter, described below or in a direct contact therewith.

The monitor may be connected to an external power source of electric power. The source power may come from any one of an electric power grid through an electrical outlet, an energy storage device such as a battery or a fuel cell, a generator, an alternator, a solar power converter, a wind energy converter and the like power sources. The connection to the external power source, for example such as electric outlet, may include a cable that is fixed (secured) to the housing and extends therefrom. The connection to the external power source may include a socket in the peripheral wall and that is accessible from an exterior surface of the housing. The connection to the external power source may include the socket and a cable that may be selectively plugged into the socket. For example, a range of input voltage from 8.5V to 16V DC can be used to make more flexible the monitor and/or adapter with existing power sources, and yet still help prevent device damage/improper function. Additionally, power topology changes, such as a battery path shutoff, may be used to better control behavior for cases involving higher than expected battery voltages. Further, preferably, to accommodate unregulated power supplies, if used, the monitor and adapter can have internal regulators to control the varying input voltage and help prevent device damage/improper function.

The monitor may be designed with an internal source of electric power, such as a battery. In this design, the battery may be selectively insertable into a battery holder disposed within the hollow interior and removable therefrom through a battery opening in the peripheral wall. The battery holder is integrated into the monitor housing and supports one or more batteries. The batteries may be AA batteries. Four AA batteries may be connected in series configuration for an effective battery voltage ranging from 6V to 3.45V. Power from batteries is provided to the controller via wire leads connected to the battery holder electrodes. The maximum voltage may be varied depending on the manufacturer and series of the batteries. A battery cover may be then provided to selectively cover and expose the battery opening. In other words, the monitor housing includes an opening through a thickness of the peripheral wall, where the opening is sized and shaped to selectively receive the battery therethrough.

The user interface includes inputs, including user operable inputs. Examples of such user operable inputs may include one of a power switch, a nurse call switch, an alarm mode switch, a tone switch, a volume switch, a record switch, and any combinations thereof. An optional delay switch may be also provided. Any switch may be provided as a pushbutton or button switch. It will be understood that user interface will include openings through a thickness of the peripheral wall of the housing so as to mount and access various switches.

The pushbutton connection may be designed as through-hole pads grouped in two sets, one with four contacts requiring six pads, and a set with a single contact requiring two pads. The set of four contacts are electrode contacts on a printed circuit board (PCB) with a six-conductor ribbon cable to provide the connection to the monitor controller. The single contact is a PCB with one electrode contact and two wire leads to connect to the monitor controller. The contacts on both PCBs may be closed via corresponding conductors embedded in molded covers. Any switch may be provided as a slide-type switch. Any switch may be provided as a toggle switch. A switch cover may be also provided to at least prevent unintended activation or deactivation of the above described inputs.

The power switch is disposed in a path of electric power to the monitor for controlling power to electronics of the monitor, such as a processor or controller as described herein, by turning the monitor device on or off. The power switch connection may include two through-hole pads to which a panel-mounted slide switch's wire leads are be soldered. The power switch will close or open the power path depending on the position of the switch. The power switch may be configured to allow actuation by hand, such as a finger sliding a manual electric switch, without requiring a tool. The power switch may be disposed on the back of the housing, in the recess, so that the power switch is completely covered by a support mechanism, and therefore completely inaccessible by any person, when mounted to the support mechanism. When the power switch is located in the recess, an accidental deactivation of this switch is prevented. A voltage regulator may be electrically connected between the power source and the monitor controller to aid in monitoring battery voltage level. Voltage regulator regulates voltage supply from the batteries or AC power source (adapter). Voltage regulator may be used to monitor battery voltage. Battery monitoring may be also provided by a separate voltage regulator.

The nurse call switch may be of a manual two-state sliding type for configuring the nurse call port to operate normally open ("NO"), when a switch slider is in one position, or normally closed ("NC") when the switch slider is in another position. The nurse call port circuit may be designed with an audio phone jack compatible with a nurse call system. When provided, the optional delay switch may be a sliding manual electric switch for configuring a delay which must be met before a sensed deactivation at a patient sensor can cause an alarm, such as 0 (no delay), 1 second or 2 seconds. The alarm mode button configures a type of alarm which occurs when a sensed deactivation at a patient sensor occurs, such as a playback of a recorded voice and an audible tone, playback of the recorded voice only, the audible tone only, or mute. The tone button configures a different types of audible alarm tones, such as for distinguishing between different monitors. The volume button configures a volume of the alarm, such as low, medium or high. The record button is used to record a voiced statement for playback during an alarm.

The battery cover may be positioned below the power switch, for covering a battery compartment containing batteries for powering the monitor, can also be disposed in the recess, so that the batteries are also completely inaccessible by any person when mounted to the support mechanism.

The user interface may include a debug port. This port is used for loading monitor controller firmware and performing diagnostics. The monitor controller may be designed and programmed to allow user to download updated/revised program (executable instructions) through the debug port. In other words, the debug port may be used as a data carrier signal that carries a program to the monitor controller.

Monitor may be designed with a diagnostic port to allow troubleshooting of the monitor when connected to a computer or any other device designed to determine a health of the monitor and/or troubleshoot. In other words, the diagnostic port may be used as a data carrier signal that carries a program to the monitor controller. The diagnostic port may be also used as the data carrier signal to upload, for example from a cloud or a server, a program to the monitor controller that was initially installed without imbedded program. Thus, the monitor controller may be configured in the field or after installation for use with a specific sensor. The diagnostic port may not be a component of the user interface.

The user interface may include outputs. The outputs may include one of a visual annunciation, an audible annunciation and a combination thereof. Visual annunciation may be designed to indicate a status of the sensor. Visual sensor annunciation may include an indicator viewable from the exterior surface of the housing. Such indicator may be lit when a connection with the senor has been established during pairing. Such indicator may be referred to as a sensor pairing status indicator. When monitor is designed to pair up with more than one sensor, a separate sensor pairing status indicator will be provided for each sensor. In this design, monitor controller will be programmed to discriminate between different sensors based on the unique sensor identifier.

The indicator may be provided to indicate a status of the monitor. Such indicator may be referred to as a monitor status indicator. Such monitor status indicator may indicate by different color various modes of operation of the monitor, such as illuminating a relatively slower (slow) flashing green to indicate a "monitor mode" in which a connected sensor is being monitored for a deactivation, illuminating a relatively faster (fast or rapid) flashing red to indicate an "alarm mode" in which an alarm is active following a deactivation detected in the monitor mode and/or illuminating a relatively slower (slow) flashing yellow to indicate a "standby mode" in which the alarm is inactive. Indicator may be designed as a light emitting diode (LED). LED may be a single color LED. LED may be a multi-color LED. An LED driver is integrated into the monitor controller and may include fade and blinking functionality.

When the monitor includes the internal battery, the indicator may be electrically connected to indicate charge level of the battery. The battery level indicator can indicate a status or charge of batteries powering the monitor, such as when disconnected from a wired power source, such as by flashing red when the battery is low (for example, below 20% charge, or a determination of a predetermined number of days of charge remaining, such as less than three days of charge remaining). This essentially simplifies readability of the device. Visual indicators may include any combinations of the indicators described above.

The user interface may include a microphone. The microphone connection may be designed as two through-hole pads to which the wire leads from a panel-mounted condenser microphone are soldered. A microphone pre-amplifier may be used to provide signal conditioning for the audio signal captured by the microphone. Its analog output is connected to an ADC input on the MCU. The microphone can be used to record a statement which could be played back through the speaker ("audio cue" or "audible cue"), such as a recorded statement played to a patient to return to the sensor when alarming. The monitor may ensure a good statement or input is recorded (non-accidental) for the audio cue by requiring all recordings be of at least a minimum duration, such as 3 seconds, to properly register the recording as a recorded statement for audio cues. The user interface may include a speaker. The speaker may be used to sound an alarm, such as an audible tone and/or playback of the recorded statement, and/or can be used to play audible cues, such as instructions for setting up the monitor, instructions for resolving an alarm condition, indication of connection or disconnection of a patient sensor or nurse call, and the like. The user interface may include a speaker and a microphone. It would be understood that the speaker and microphone will be connected to the controller through a respective interface circuit. The speaker interface circuit may include a speaker driver. Speaker driver may be provided as a class AB mono amplifier. Speaker connection may be designed as two through-hole pads to which the wire leads from a panel-mounted mylar speaker are soldered. The microphone interface circuit may include a microphone pre-amplifier circuit. The speaker and/or the microphone may be provided separately from the user interface. Accordingly, the monitor may be designed to output a reason for the alarm, after user presses the hold button. For example, the monitor may output "alarm paused" when user presses hold button. The monitor may be designed to output, with an audio cue, which sensor has low battery ("bed sensor battery low") to make it easy to replace the right sensor and not waste money replacing one that doesn't have a low battery. Further in this regard, for example, the monitoring system can include a plurality of sensor-adapters and the signal can define at least one of the plurality of sensor-adapters has a condition such as (i) a low battery and/or (ii) a lost communication signal. In such a case, preferably, the monitor can receive the signal and then provides a notification to the caregiver. And, even more preferably, the notification can be specific to the condition of the low battery or the lost communication signal.

Communication interface within the monitor may include at least one transceiver, that communicates using any of the 802 standards of the Institute of Electrical and Electronics Engineers (IEEE), such as, but not limited to, 802.11 (WiFi®), 802.15.1 (Bluetooth®), and/or 802.15.4 (Zig-Bee®).

When the sensor is designed to sense a presence or an absence of a person under at least a partial watch of a caregiver, the monitor may be adapted with a wired connection to a remote location where such caregiver may be situated. In a hospital environment, such person will be referred to as a patient and caregiver may be referred to as a nurse. In such hospital environment, the wired connection may be between a nurse call port accessible from an exterior surface of the monitor that and a nurse call jack (socket) that is generally positioned in a proximity to a patient bed.

The monitor may be designed such that a sequence of inputs may be used to configure a nurse call connection, so that this cannot be done accidently, when the monitor is in the wired connection between the nurse call port and the nurse call jack. In a non-limited example, a sequence of activating a mode switch and a tone switch may be used to configure such nurse call connection. The monitor may be designed with a nurse call configuration and latching call circuit. In this circuit, a relay may be electrically connected between the monitor controller and the nurse call port. A coil in this relay is electrically connected through the controller with the nurse call switch in a nurse call circuit. The nurse call switch is set either in NO position or NC position based on a type of the connected nurse call system. Thus, the nurse call switch operates to provide an input to the controller that defines a default (off) state for the relay. With a NO type nurse call system, the relay is connected to define an open-circuit by default, and a closed-circuit only when a nurse call is intended to be triggered. With a NC type nurse call system, the relay is connected to define closed-circuit by default, and open-circuit only when a nurse call is intended to be triggered. The nurse call switch circuit is thus designed depending on the type of nurse call system being connected to the monitor, where the nurse call switch opens or closes the circuit. It is to be understood that a nurse call signal may not be generated by the nurse call switch directly, it just makes or breaks a circuit whose state is detectable by the connected nurse call system. The making or breaking of the nurse call circuit is what results in a nurse call.

The relay may be provided with two coils and a contact that is electrically connected with the nurse call port. The nurse call circuit may be designed such that one (first) coil is energized to close the contact, closing the nurse call circuit and another (second) coil is energized to open the contact, opening the nurse call circuit. In more details the first coil may be energized in any one of the following operating conditions: the nurse call switch is set to NO position and patient sensing signal from the sensor is lost; the nurse call switch is set to NC position and monitor intends to terminate nurse call signal (patient has returned and/or alarm has been serviced, or power cycle has occurred); and the nurse call switch setting is changed to NC position from NO position. The second coil may be energized in any one of the following operating conditions: the nurse call switch is set to NC position and patient sensing signal from the sensor is lost; the nurse call switch is set to NO position and monitor intends to terminate nurse call signal (patient has returned and/or alarm has been serviced, or power cycle has occurred); and the nurse call switch setting is changed to NO position from NC position. The use of the relay with two coils defines a latched nurse call circuit where each coil is momentarily energized based on the position of the nurse call switch. Once the coil is energized and the relay contact either closes or opens, no additional current draw is needed for operability of the nurse call circuit. The latching condition further extends battery life as compared with circuits where continuous current draw is required to operate the nurse call circuit. The latched nurse call circuit may be also designed as a transistor circuit. The latched nurse call circuit may be also designed as a circuit that translates voltage of the digital output. Monitor design with the nurse call circuit, as described above, provides a flexibility to choose wired or wireless connection to the nurse call jack.

The present disclosure also provides a sensor that is designed to sense a presence or an absence of a person. The sensor is also designed to communicate with the monitor, as described above. The sensor may be designed as a pressure sensitive pad with an electrical circuit and a neck portion. The neck portion may have an end with an opening to allow air flow. The neck portion may be a closed neck portion with a hollow interior and a vent. The vent may be designed as one or more slits through a wall thickness of the neck portion. The vent may be designed as one or more apertures through a wall thickness of the neck portion. A sensor controller is disposed within the neck portion. The sensor controller is mechanically and electrically connected to the conductive elements within the electrical circuit. The sensor controller may be installed in a direct connection with the conductive elements. In this direct connection, the sensor does not require use of mating connectors. When the sensor controller is installed in the closed neck portion, the sensor controller may include a wired connection with electrically conductive ink grids to be described later in this document. The wired connection may include a connector. The vent may be aligned with a sensor controller. The vent may be positioned in an area adjacent to an area occupied by the sensor controller.

The pressure pad may comprise a multilayer pressure sensitive pad formed by three layers, disposed in a series with each other, and defining two outer layers and one middle layer, all layers being enclosed in a cover. Each outer layer from two outer layers may be electrically conductive with a grid made of conductive ink on one surface of the outer layer. The grids of electrically conductive ink may be referred to as a first grid and a second grid. The other surface of each layer may be non-conductive and have no ink. The middle layer may comprise a non-conductive compressible and resilient material with a plurality of apertures through a thickness of such compressible and resilient material. The plurality of apertures may define a grid of apertures. The compressible and resilient material may include foam. When the middle layer is manufactured from a compressible and resilient material with a grid of apertures through a thickness of the compressible and resilient material, the apertures enable a contact between the conductive ink on the first grid and the conductive ink on the second grid when a pressure being applied to an exterior surface of the cover, compressing the compressible and resilient material and forcing the first and second outer layers to move toward each other. The controller may be installed in a direct mechanical connection with each conductive ink grid. In this connection both the sensor controller and the conductive ink grid may be designed with apertures that are aligned with each other during assembly and a fastener is used to mechanically fasten the sensor controller and the conductive ink grid therebetween. The fastener may be a rivet.

One outer layer may be referred to as a first conductive layer. The other outer layer may be referred to as a second conductive layer. Thus, the first conductive layer and second conductive layer contact each other, through the apertures in the non-conductive middle layer, when a pressure is applied to one of the first and second conductive layers causing the non-conductive middle layer to compress. When the first conductive layer and second conductive layer contact each other, the sensor controller outputs an electrical signal defining the contact.

When pressure is applied to an exterior surface of the pressure sensitive pad, and respectively to the sensor controller, the conductive grids of the outer layers may be in contact with each other, and the resistance between the conductive layers can be measured. As such contact area increases (through the plurality of apertures of the middle layer), the resistance between the outer layers decreases. When there is no pressure on the sensor, the conductive grids of the outer layers are not in contact and therefore an open circuit occurs. In other words, the conductive grids of the outer layers function (or configured) to measure resistance for sensing.

The sensor controller may comprise a programmable nonvolatile (non-transitory) memory and one or more microprocessors. The sensor controller may be referred to as a sensor circuit. The sensor controller is connected to the conductive grid of one or both outer layers.

The sensor controller may be programmed to wirelessly communicate battery status to the monitor controller. The sensor controller may be mounted within the neck portion of the sensor. When the opening in the neck portion is designed to remain open during operation of the sensor, the sensor controller may be sized and shaped to maintain the opening in the open condition.

During operation, a resistance of the outer layers may be measured and may be stored in the memory of the sensor controller and/or memory of the monitor controller. The monitor controller may send a signal to the sensor controller to read the resistance stored in the memory of the sensor controller. The monitor controller may be designed to read the resistance value stored in the memory of the monitor controller. The resistance value may be measured as a contact between the outer layers. The resistance value may be measured as a loss of contact between the outer layers. The resistance value may be measured incrementally in applications where pressure may be applied only to a portion of the sensor or may change. The resistance value may define one of a pressure sensing condition and a non-pressure sensing condition. As a non-limiting example, a person sitting on the pressure sensitive pad and leaning in a forward direction may not contact the entire portion of the pressure sensitive pad, thus reducing the contact between the outer layers.

When the sensor is electrically and physically connected to the monitor, the electrical signal is transmitted to the monitor over a wired connection. When the sensor is wirelessly paired up with the monitor and is being in a wireless connection therewith, the signal is transmitted to the monitor by way of a wireless connection. The wireless connection may include a wireless radio frequency (RF) communication.

The sensor controller may be designed as an RFID tag. Accordingly, the circuit within the monitor may be designed as RFID reader. The circuits within the sensor and monitor may be designed to operate on a Bluetooth® wireless technology. The circuits within the sensor and monitor may be designed to operate on near field communication (NFC) technology. Thus, the sensor controller may be designed to wirelessly pair with the monitor in a first wireless mode and wirelessly communicate with the (remote) monitor in a second wireless mode. The first mode may include NFC circuit. The first mode may include a short distance wireless communication, for example such as BLE. The second mode may include a short distance wireless communication, for example such as BLE. NFC circuit may be designed to wake-up the sensor controller from sleep (to conserve energy) and pair out-of-band (OOB). In a wireless communication, the sensor controller includes one or more antennas. The antenna may be designed as trace on a PCB. The antenna, for example such as a helical antenna, may be connected to the PCB. A transceiver, for example such as Nordic Semiconductor NRF52832-QFAB-R transceiver, may function as the controller for the sensor. It has built-in Bluetooth® and NFC Tag functionality leveraged as part of the Wireless Platform core features. Its NFC coil is connected via wires to dedicated through-hole pads while its Bluetooth® antenna is planer inverted-F antenna designed into the PCB. The transceiver may include a processor, a memory, a power supply, an input/output (I/O) interface, a near field communication (NFC) circuit, and a short distance wireless communication circuit. A battery holder may be provided to power the sensor controller by a lithium coin cell battery. A voltage regulator may be electrically connected to the battery holder. Thus, the voltage regulator will be electrically connected mediate the battery and the transceiver.

As described above, the sensor may be designed to include a first conductive layer, a second conductive layer, a non-conductive middle layer disposed between the first and second conductive layer, a cover enclosing the first conductive layer, the second conductive layer and the non-conductive middle layer, the cover defining a neck portion with an open end, a sensor circuit disposed within the neck portion, the sensor circuit being electrically connected to each of the first and second conductive layers, and a spacer positioned between the sensor circuit and an interior surface of the neck portion. The sensor may be provided with a pairing alignment mark on an exterior surface of the pad for alignment, during pairing, with a pairing alignment mark disposed adjacent antenna in the monitor.

As described above, the sensor may be designed to include a first outer layer comprising an interior surface, a second outer layer comprising an interior surface, a middle layer disposed between the interior surface of the first and second outer layers, a first grid with a conductive ink on the interior surface of the first outer layer, a second grid with the conductive ink on the interior surface of the second outer layer, a cover enclosing the first outer layer, the second outer layer and the middle layer, the cover defining a neck portion with an open end, a sensor controller disposed within the neck portion, the sensor controller comprising an electrical connection with each of the conductive ink on the interior surface of the first outer layer and conductive ink on the interior surface of the second outer layer, and spacer positioned between the sensor controller and an interior surface of the neck portion. The spacer may be employed to maintain the opening in the open condition. The spacer may be designed to cushion contact between the person and the neck portion. Two spacers may be also provided, with the sensor controller being located therebetween.

As described above, the sensor controller may be designed with one or more processors and a memory that is not a transitory propagating signal. The memory being connected to the one or more processors and encoding computer readable instructions, including processor executable program instructions. The computer readable instructions are accessible to the one or more processors, wherein the processor executable program instructions, when executed by the one or more processors, cause the one or more processors to perform operations at least including wirelessly pairing the sensor to the monitor, wirelessly transmitting a first electrical resistance value defining a deactivated condition when the first grid is spaced apart, by the middle layer, from the second grid, and wirelessly transmitting a second electrical resistance value defining an activated condition when the first grid contacts the second grid. The operations may further include wirelessly transmitting a battery level in the sensor circuit. The operations may further include wirelessly transmitting one of a sensor type, a unique sensor identifier and a combination thereof.

The sensor controller may be designed (programmed) to receive a status request from the monitor and transmit a status response only and only in a response to a receipt of the status request. In other words, the sensor controller will not transmit any information related to contact or lack thereof between outer layer, remaining or used battery life, health of various circuits within the sensor controller or other information without a receipt of a signal from the monitor controller asking for such information.

Prior to sensor disposal, sensor controller may be removed by simply cutting a portion of the pouch and/or neck with scissors or a knife.

The present disclosure also provides an adapter that is designed to couple a monitor and a sensor to a remote location by way of a wired communication. The adapter may be designed to integrate with the monitor as described above and the sensor as described above.

The adapter is designed with a housing, an adapter controller and a plug sized and shaped to be received within a socket connected to the remote location in such wired communication.

The housing incudes a peripheral wall that defines a hollow interior of the housing. The adapter controller is disposed within the hollow interior. The adapter may be coupled to an external power source, as described above in regards to the monitor. The adapter may be designed with a battery selectively insertable into a battery holder within the hollow interior and removable therefrom through a battery opening in the wall. The battery holder is integrated into the adapter housing and supports one or more batteries. The batteries may be AA batteries. Two AA batteries may be connected in series configuration for an effective battery voltage ranging from 3V to 2.1V. Power from batteries is provided to the controller via wire leads connected to the battery holder electrodes. The maximum voltage may be varied depending on the manufacturer and series of the batteries. A battery cover may be provided to selectively cover and expose the battery opening. The adapter includes a power switch that can be referred to as an ON/OFF switch. The power switch connection is two through-hole pads to which a panel-mounted slide switch's wire leads are soldered. The power switch will close or open the power path depending on the position of the switch. As has been explained above, a voltage regulator may be also provided between the battery and the adapter controller to regulate voltage supply. The same or another voltage regulator may be used to monitor battery voltage level. A status indicator may be also provided that is electrically coupled to the adapter controller and that is visible from the exterior of the housing. The status indicator may be a tri-color LED having red, green, and blue channels in a common anode configuration to indicate adapter status.

The adapter may be designed with a cable. A proximal end of the cable is coupled to the housing. The proximal end may be fixed to the adapter housing. The proximal end may be fixed with a strain relief. The proximal end may be detachably attached to the housing by way of a socket. In any form, the proximal end of the cable, and the cable itself, is electrically connected to the adapter controller. An 6.35 mm audio plug terminates a distal end of the cable. The plug being disposed, by a length of the cable, at a distance from the housing. The plug is shaped and sized to fit into a nurse call jack. Such nurse call jack may be referred to as a nurse call interface.

The adapter may be designed such that the plug extends directly from the exterior surface of the housing.

The adapter controller may be designed similar to the sensor controller as described above. The adapter controller may be designed similar to the monitor controller as described above. Such adapter controller may include the transceiver as described above. The adapter is designed to wirelessly pair with a remote monitor in a first wireless mode, as described above and wirelessly communicate with the remote monitor in a second wireless mode, as described above.

A transceiver, for example such as Nordic Semiconductor NRF52832-QFAB-R transceiver, may function as the controller for the adapter.

A monitor pairing alignment mark may be disposed on an exterior surface of the adapter housing adjacent an antenna location.

The adapter may be designed with a latched nurse call circuit as described above.

The disclosure also provides a patient monitoring apparatus that includes a monitor, as described above, an adapter, as described above, and a sensor, as described above. The sensor may be referred to as a patient sensor. The monitor is designed to wirelessly communicate with the adapter and the sensor. The adapter is designed to wirelessly communicate with the monitor and is designed to interface with a wired connection to the monitoring station. The wired connection may be provided in a patient room, generally near a patient bed. The apparatus may be referred to as a patient monitoring system.

The disclosure also provides a patient monitoring apparatus that includes a monitor, as described above, and a sensor, as described above. This monitor is designed to connect to the remote monitoring location with a plug sized and shaped to be received within nurse call interface jack (socket). In other words, the monitor and the adapter, as described above, may be integrated into a single unit, thus eliminating a need for wireless connection therebetween. This apparatus may be also referred to as a patient monitoring system.

The disclosure also provides a method of patient monitoring. The method may be achieved by pairing a sensor with a monitor, in a first wireless connection, when a first alignment mark on an exterior surface of a monitor housing is being aligned with a second alignment mark on the sensor, pairing an adapter with the monitor, in the first wireless connection, when a third alignment mark on an exterior surface of an adapter housing is being aligned with the first alignment mark, activating, at the monitor, a second wireless communication with the sensor, transmitting, with the sensor to the monitor over the second wireless connection, a first signal defining a patient sensing condition and a second signal defining a patient non-sensing condition, transmitting the second signal from the monitor to the adapter over the second wireless connection, and transmitting the second signal from the adapter to a remote monitoring station over a wired connection. Pairing the sensor with the monitor may be achieved by transmitting, using a near field communication (NFC) protocol, a sensor type and/or unique sensor identifier. Transmitting the second signal may be achieved by transmitting the second signal using a short distance wireless communication protocol. An alarm may be activated upon transmission of the second signal. When pairing, the monitor controller is also programmed to check if the sensor and/or the adapter of the same type has been previously paired and stored in the monitor controller memory. If the monitor controller determines that the monitor was previously paired with the same type of the sensor and/or the adapter, the monitor controller is programmed to disassociate with such previous devices and pair up with new sensor and/or adapter. Additionally, or alternatively, the second signal can be used to define at least one of the sensor and the adapter has a condition. This condition can be a variety of helpful queues to operation of the system, such as (i) a low battery (ii) a lost communication signal, (iii) type of sensor, (iv) previously paired connection, and other conditions as taught herein. Still further in this regard, preferably, activating the alarm includes giving specific notification to the caregiver about the type of condition in response to the monitor receiving the second signal.

The method of patient monitoring may be also achieved by pairing a sensor with a monitor, in a first wireless connection, when a first alignment mark on an exterior surface of a monitor housing is being aligned with a second alignment mark on the sensor, pairing an adapter with the monitor, in the first wireless connection, when a third alignment mark on an exterior surface of an adapter housing is being aligned with the first alignment mark, transmitting, with the sensor to the monitor over a second wireless connection, a signal defining one of a patient sensing condition and a patient non-sensing condition, transmitting the signal, defining the patient non-sensing condition, from the monitor to the adapter over the second wireless connection, and transmitting the signal, defining the patient non-sensing condition, from the adapter to a remote monitoring station over a wired connection. Transmitting the signal from the sensor to the monitor may first require receiving, at the sensor, a prompt from the monitor.

The method of patient monitoring may be also achieved by pairing a sensor with a monitor, in a first wireless connection, pairing an adapter with the monitor, in the first wireless connection, transmitting, with the sensor to the monitor over a second wireless connection, a signal defining one of a patient sensing condition and a patient non-sensing condition in a response to a prompt from the monitor, transmitting the signal, defining the patient non-sensing condition, from the monitor to the adapter over the second wireless connection, and transmitting the signal, defining the patient non-sensing condition, from the adapter to a remote monitoring station over a wired connection.

A method of patient monitoring may include a capability to monitor, with a monitor, a plurality of sensors through a combination of wireless and wired connections but where only one sensor is actively monitored.

A method of patient monitoring may include unpairing one sensor when another sensor of the same type is to be paired with the monitor. Unpairing may also include using the hold switch to temporarily place the monitor into a hold mode. Preferably, for example, this step can be accomplished through use of single button activation, such as the MODE switch, aka a MODE button. Additionally, and most preferably, such unpairing, even when so easy to accomplish, will not occur for any sensor that is being actively monitored, for obvious safety reasons. Alternately, or additionally, the unpairing can be accomplished through use of the OFF switch and/or the sensor going out of range, and again, preferably only for not actively being monitored sensors.

A method of patient monitoring may include an attempt to automatically reconnect (i.e., repair) the sensor and the monitor when a communication signal therebetween is lost. For example, a logic loop (not shown) can be employed that assesses if the sensor(s) is connected to the monitor. In the event of lost communication therebetween, the monitor can first provide a visual and/or audio notification to alert the caregiver that action is needed by the caregiver, and preferably including which sensor(s) is needing to reconnect. Then, while awaiting caregiver attention, the sensor(s) will automatically attempt to reconnect to the monitor. For example, the first wireless transceiver can attempt to reconnect with the second wireless transceiver if the first wireless transceiver and the second wireless transceiver lose communication therebetween. This reconnect attempt preferably does not require movement of the patient, and thus avoids having to manually pair up, or move in close proximity to each other, the sensor with the monitor again, at least during this automatic reconnect phase. The reconnect duration may be terminated after a selected time period so as to conserve sensor battery. Additionally, or alternately, the adapter can employ this same functionality, in essentially the same way, but to help with reconnection between the adapter and the monitor whenever it is lost therebetween.

If a computer is used to upload the program, the program may be implemented in the form of software stored on a computer-readable non-transitory information storage medium such as an optical recording media (e.g., CD-ROMs, or DVDs) or magnetic storage media (e.g., ROM, RAM, USB, floppy disks, hard disks, etc.). The information storage medium may be an internal part of the computer, a removable external element coupled to the computer, or unit that is remotely accessible via a wired or wireless network. The non-transitory computer-readable recording medium may include program instructions, data files, and data structures, alone or in a combination thereof.

Such program, provided on a non-transitory computer-readable storage medium, may cause a processor within a monitor controller to execute pairing with a sensor, in a first wireless connection, when a first alignment mark on an exterior surface of a monitor housing is being aligned with a second alignment mark on the sensor, pairing with an adapter, in the first wireless connection, when a third alignment mark on an exterior surface of an adapter housing is being aligned with the first alignment mark, activating a second wireless communication with the sensor and/or monitor, receiving, a first signal defining a patient sensing condition and a second signal defining a patient non-sensing condition, and transmitting the second signal to the adapter over the second wireless connection.

In the above described apparatus, pairing between the monitor and the sensor or between the monitor and the adapter only requires holding two devices near each other and wait for the monitor to indicate pairing. Pairing may be indicated by an audible message through the speaker. Pairing may be indicated by a lit sensor indicator. No removal of keys, additional steps, for example such as pressing a button on the monitor, is required. In other words, pairing is provided as a one-step operation, including unpairing of a previously paired sensor and/or adapter without any additional efforts by the user. Use of NFC may provide a more secure pairing.

Wireless communication between the monitor with sensor and monitor with adapter eliminates cords that potentially can create a tripping hazard and allowing the monitor to be placed anywhere in the room. Wireless communication also allows ease of pairing by easily moving monitor to the sensor and/or adapter or moving the sensor and/or adapter to the monitor. Yet, the monitor may incorporate use of existing sensors that may not be equipped with wireless communication.

The apparatus may be designed for use in healthcare facilities, including hospitals, clinics, hospices and the like.

The apparatus may be designed for use in nursing homes.

The apparatus may be designed for use in a home environment to assist caregivers and/or family members of elderly people.

This document also incorporates herein by reference and in their entirety disclosures of U.S. Pat. No. 10,692,346 B2, titled "Electronic Fall Monitoring System" and issued on Jun. 23, 2020 and Pub. No. US 2020/0320843 titled "Electronic Fall Monitoring System" and published on Oct. 8, 2020, both owned by the Applicant.

Now in a further reference to the Figures:

FIG. 1 illustrates a front view of a monitor 12. The microphone 14 and speaker 16 are illustrated as being positioned on the peripheral wall 22a of the housing 22 with the hollow interior 22b. A status indicator 18 and a battery level indicator 20 are located toward a top of the housing 22 of FIG. 1, adjacent a hold switch 54. Sensor indicators 17a, 17b and 17c are shown adjacent the speaker 16 but may be disposed anywhere on the peripheral wall 22a. The pairing alignment mark 27 is illustrated as a graphical item but can be provided as text.

Figure 2:
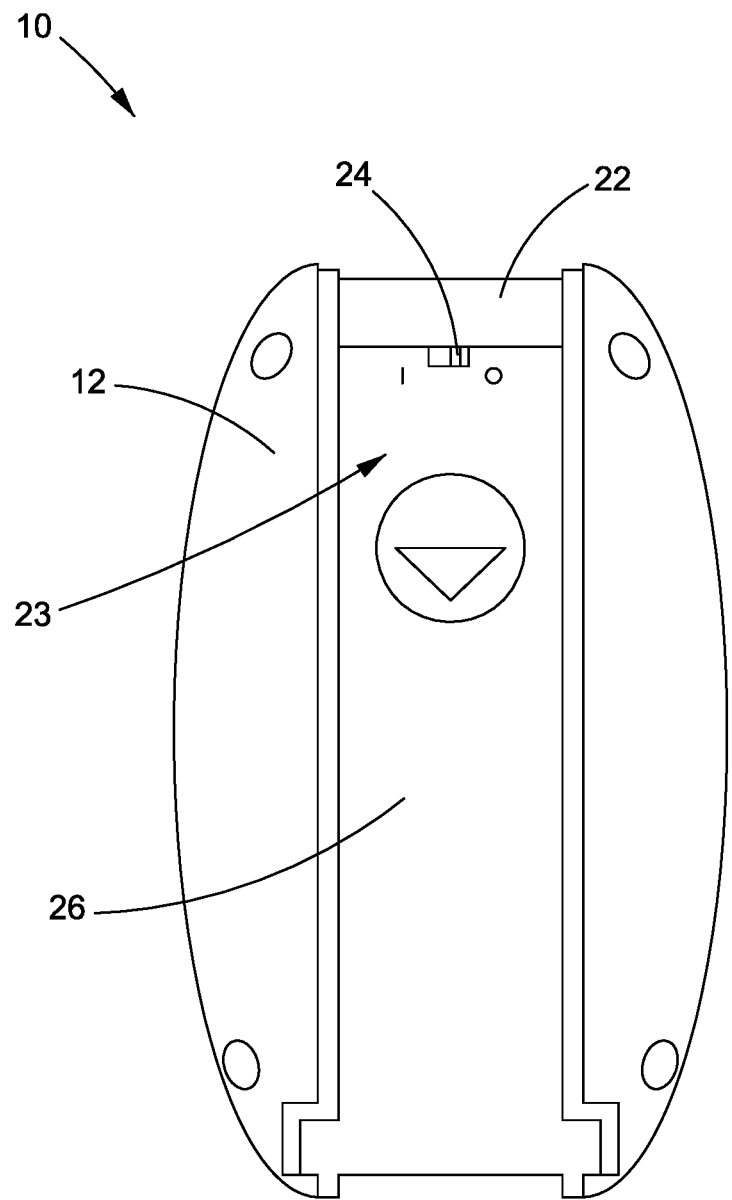
FIG. 2 illustrates a rear view of the monitor.

FIG. 2 illustrates a rear view of the monitor 10 where a recess 23 is located below the power switch 24 with the battery cover 26 being also shown as located within the recess.

Figure 3:
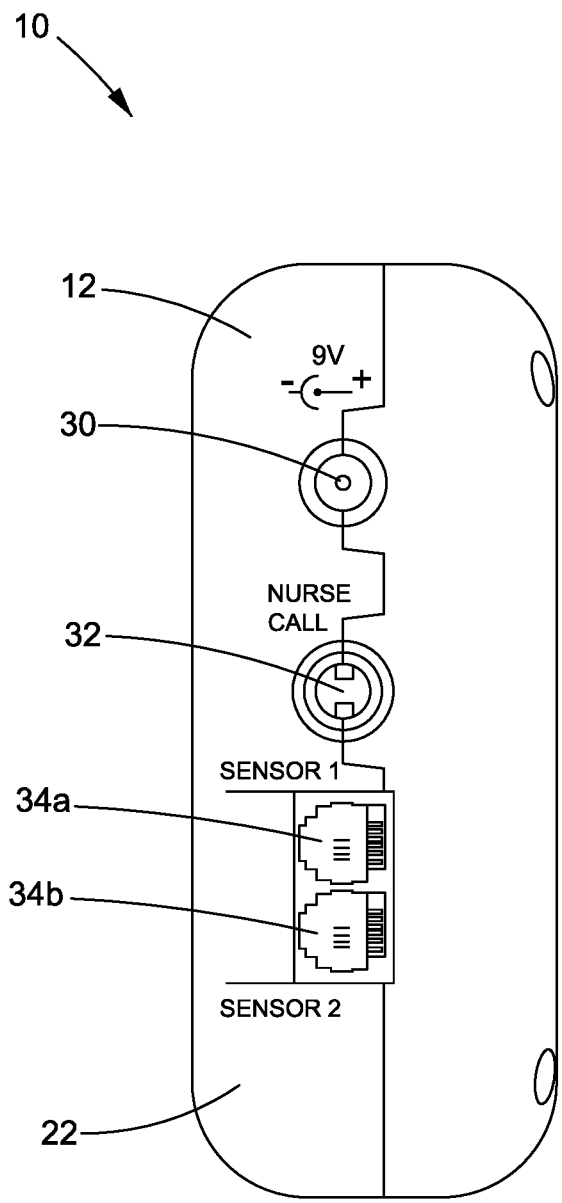
FIG. 3 illustrates a side view of the monitor.

FIG. 3 illustrates a side view of the monitor and, more particularly illustrates including a power port 30 for connecting to a wired AC power source, a nurse call port 32 for connecting to a nurse's station (not shown), and multiple wired patient sensor ports 34, such as first and second sensor ports 34a and 34b, also identified as "Sensor 1" and "Sensor 2," respectively, shown as RJ connectors.

Figure 4:
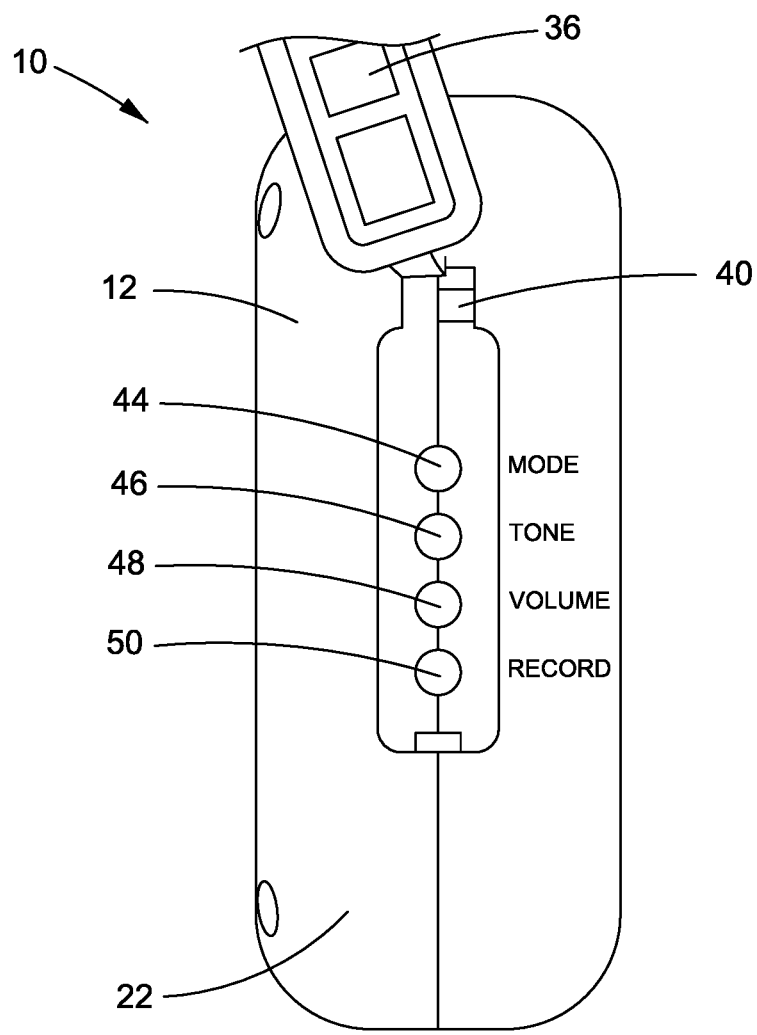
FIG. 4 illustrates a side view of the monitor.

FIG. 4 illustrates a side view of the monitor and, more particularly illustrates a housing cover 36 to cover or shield the configuration inputs when not in use, a sliding manual electric nurse call switch 40, an alarm mode button 44, a tone button 46, a volume button 48 and a record button 50.

Figure 5:
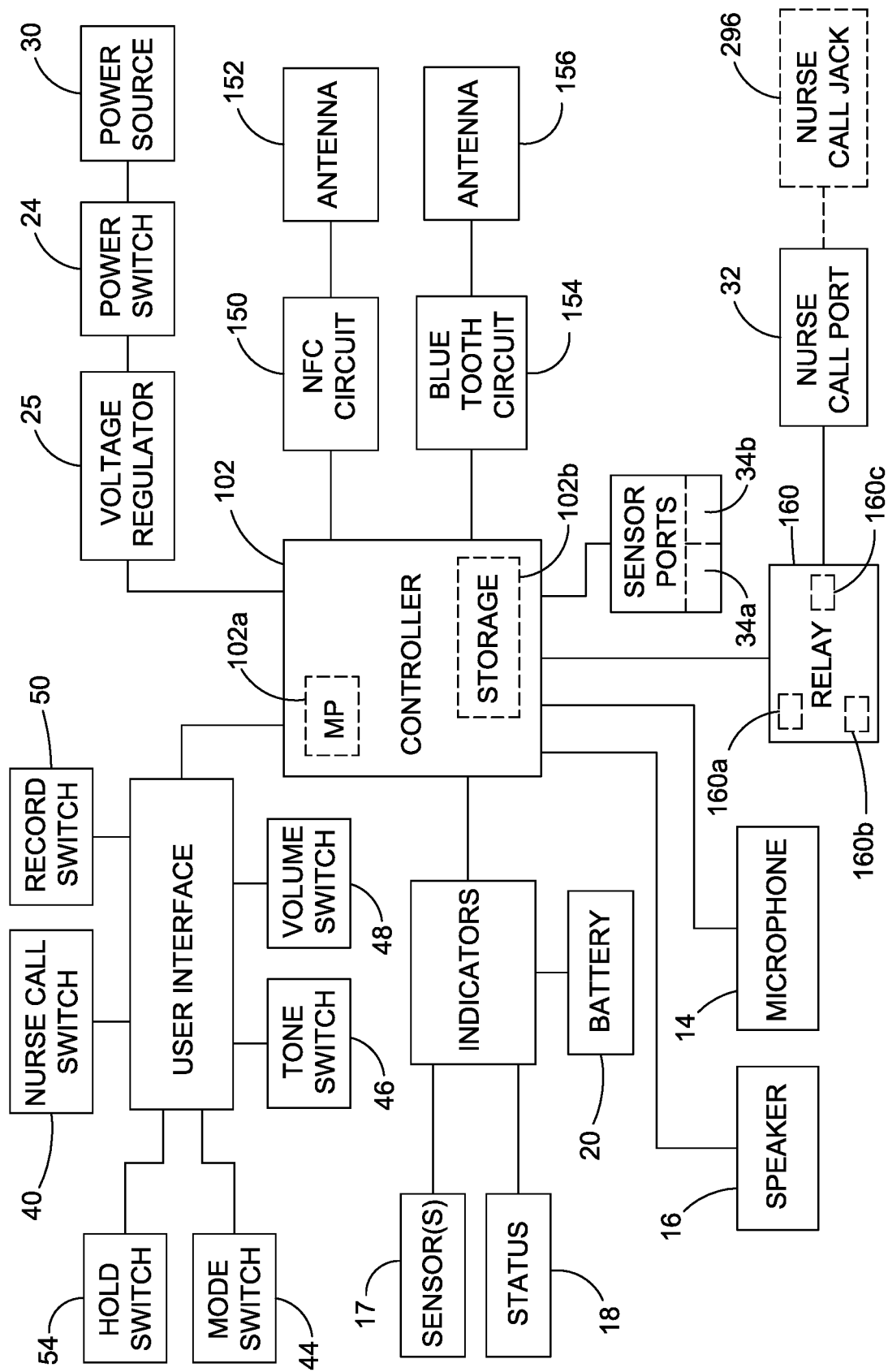
FIG. 5 illustrates a block diagram of the monitor.
Figure 6:
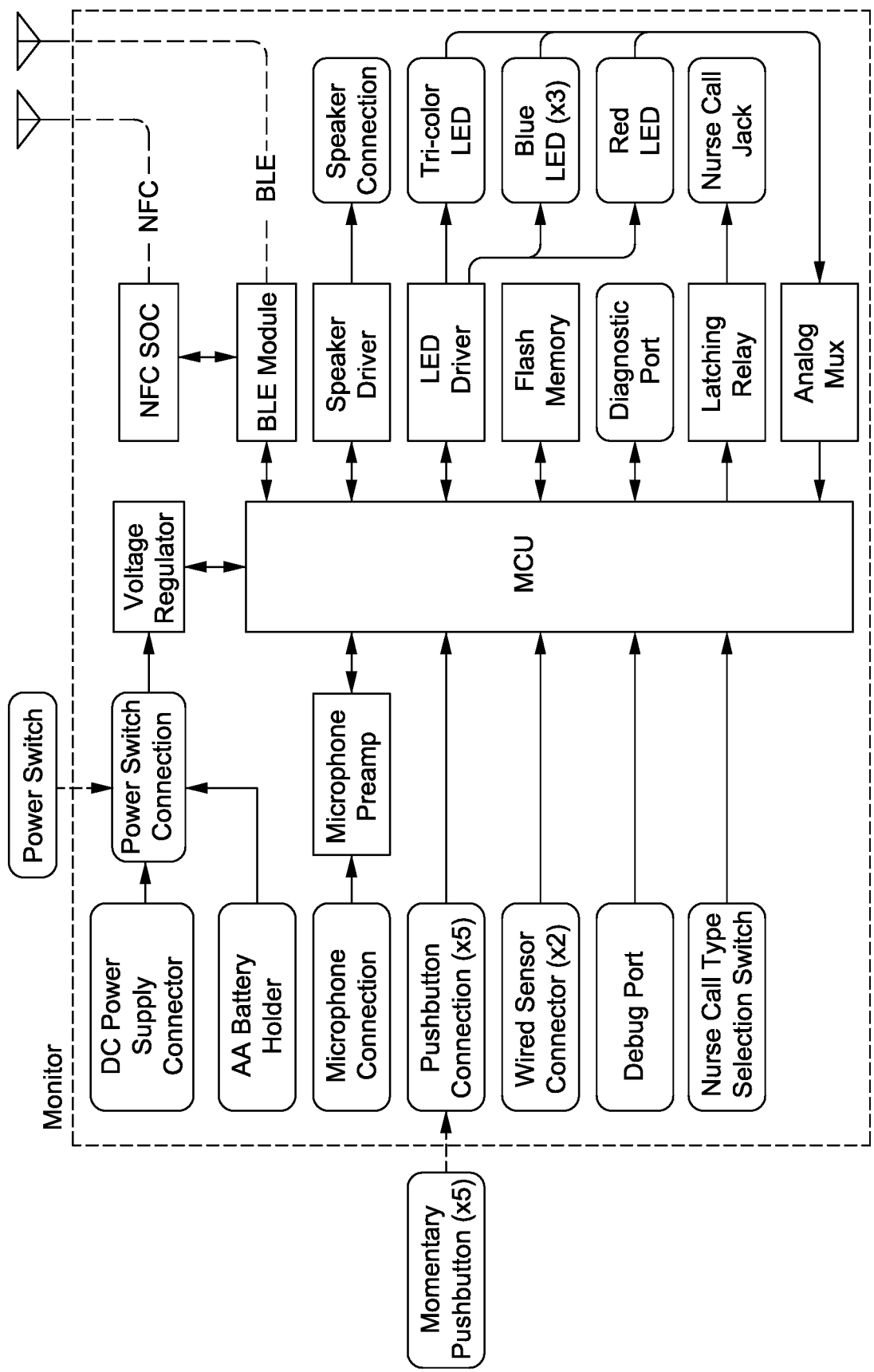
FIG. 6 illustrates a hardware architecture of the monitor.

FIG. 5 illustrates a block diagram of the monitor 10 and FIG. 6 illustrates a hardware architecture of the monitor 10. In addition to the above described components in FIGS. 1-4, FIG. 5 also illustrates a monitor controller 102 with a processor 102a and memory 102b, NFC circuit/module 150 having a connection with antenna 152, and a Bluetooth® circuit/module 154 having a connection with antenna 156. A relay 160 is disposed mediate the monitor controller 102 and nurse call port 32. The nurse call port 32 is in a wired connection with the nurse call jack 296.

Figure 7:
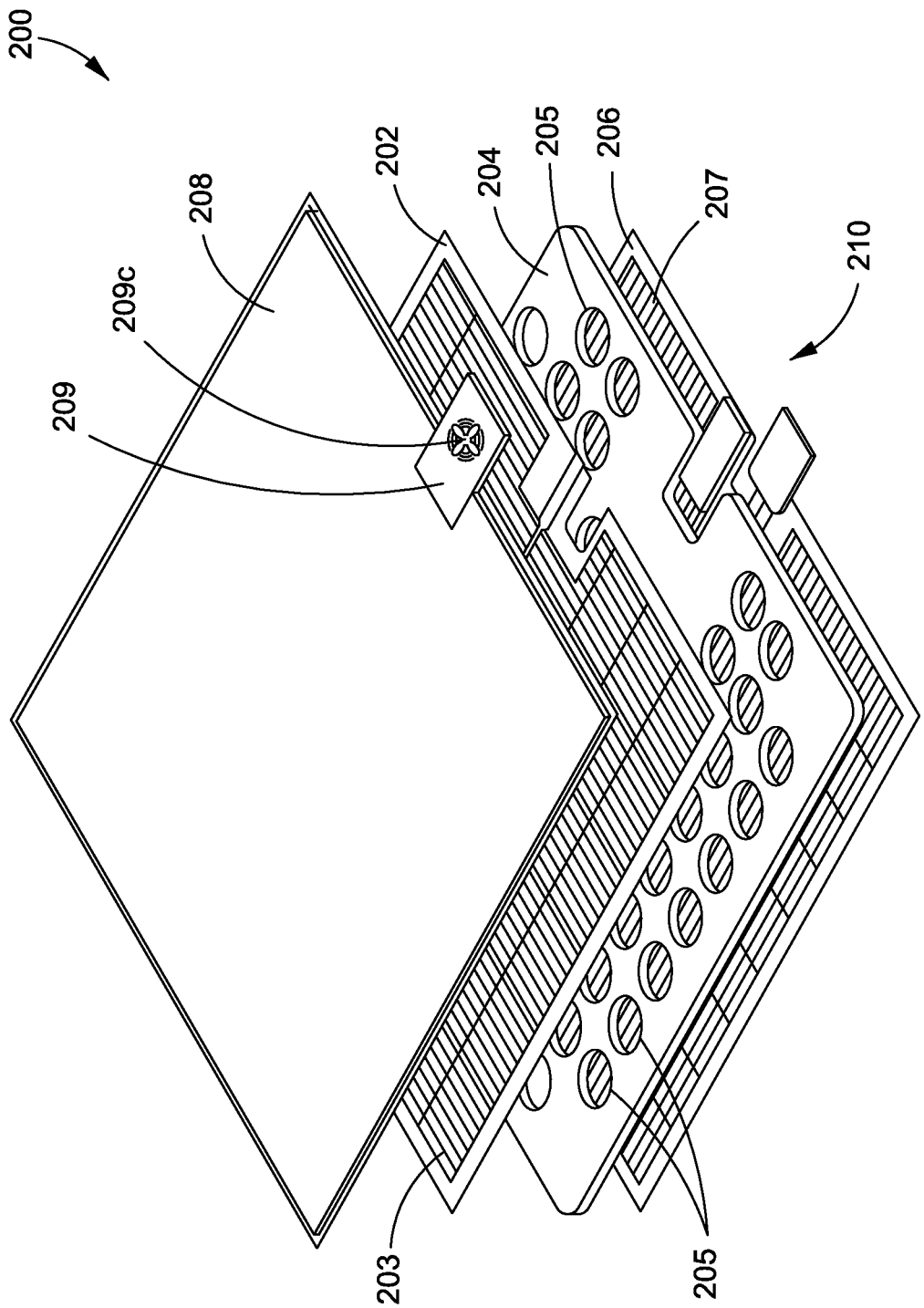
FIG. 7 illustrates an exploded view of a sensor.

FIG. 7 illustrates an exploded view of a sensor 200 with one external layer 202 with a conducting grid 203, another external layer 206 with a conducting grid 207, a middle layer 204 with a grid of apertures 205, a cover 208 with a neck portion 209 with a pairing alignment mark 209c, and a sensor controller 210.

Figure 8:
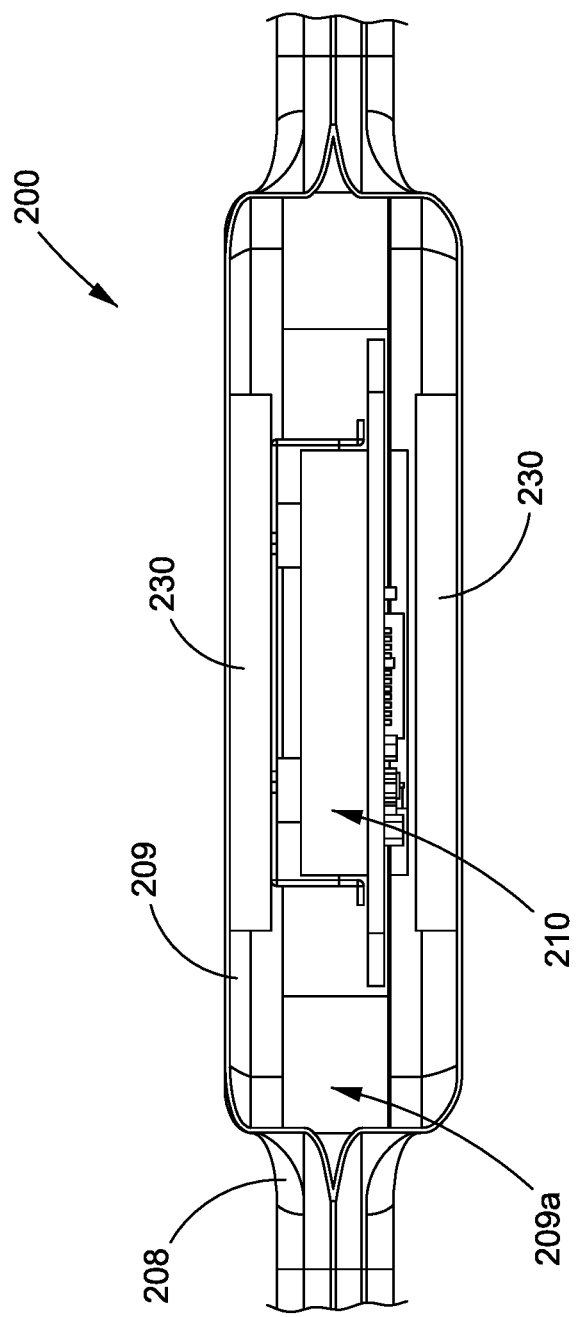
FIG. 8 illustrates a partial end view of the sensor of FIG. 7.

FIG. 8 illustrates a partial end view of the sensor 200, particularly illustrating a neck portion 209 with an opening 209a. The sensor controller 210 is also shown between two spacers 230, although one spacer 230 may be used, particularly next to the surface of the cover 208 facing the patient.

Figure 9:
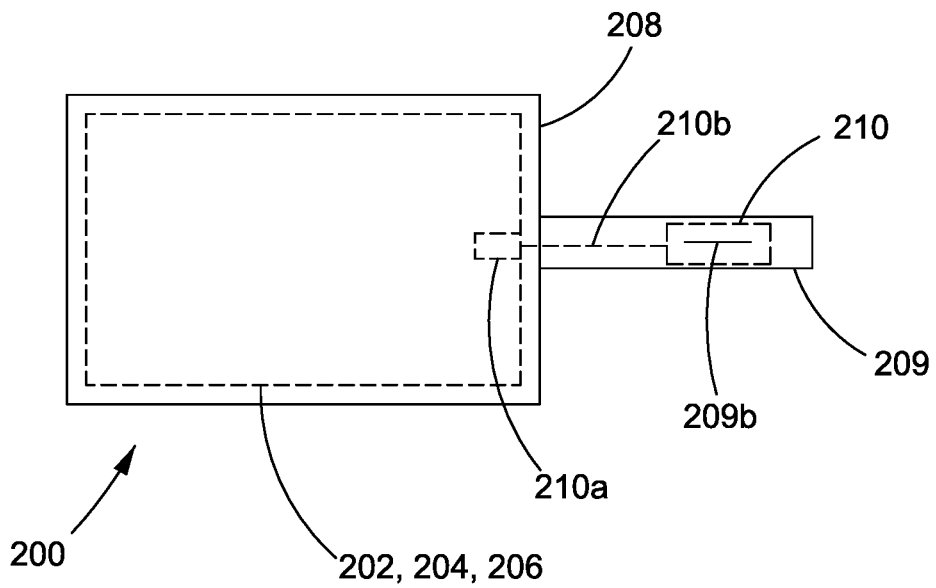
FIG. 9 illustrates a block diagram of a sensor.

FIG. 9 illustrates a diagram of the sensor 200 with the controller 201 disposed within the neck portion 209 and being connected to the electrically conductive grid with wire(s) 201b and an interface connector 201a. FIG. 9 also illustrate a vent 209b in a slit shape.

Figure 10:
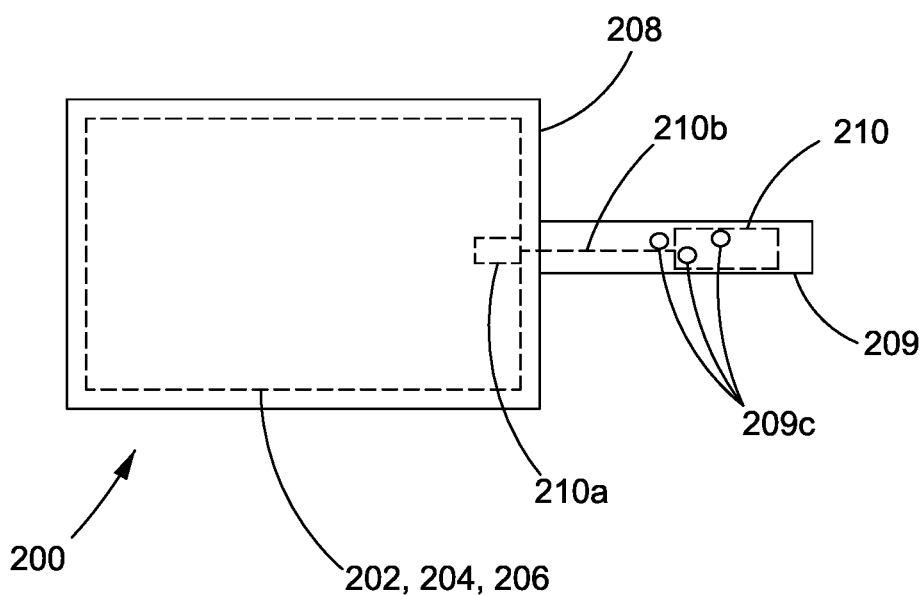
FIG. 10 illustrates a block diagram of a sensor.

FIG. 10 illustrates a diagram of the sensor 200 with the controller 201 disposed within the neck portion 209 and being connected to the electrically conductive grid with wire(s) 201b and an interface connector 201a. FIG. 10 also illustrates a vent 209c in a round aperture shape.

Figure 11:
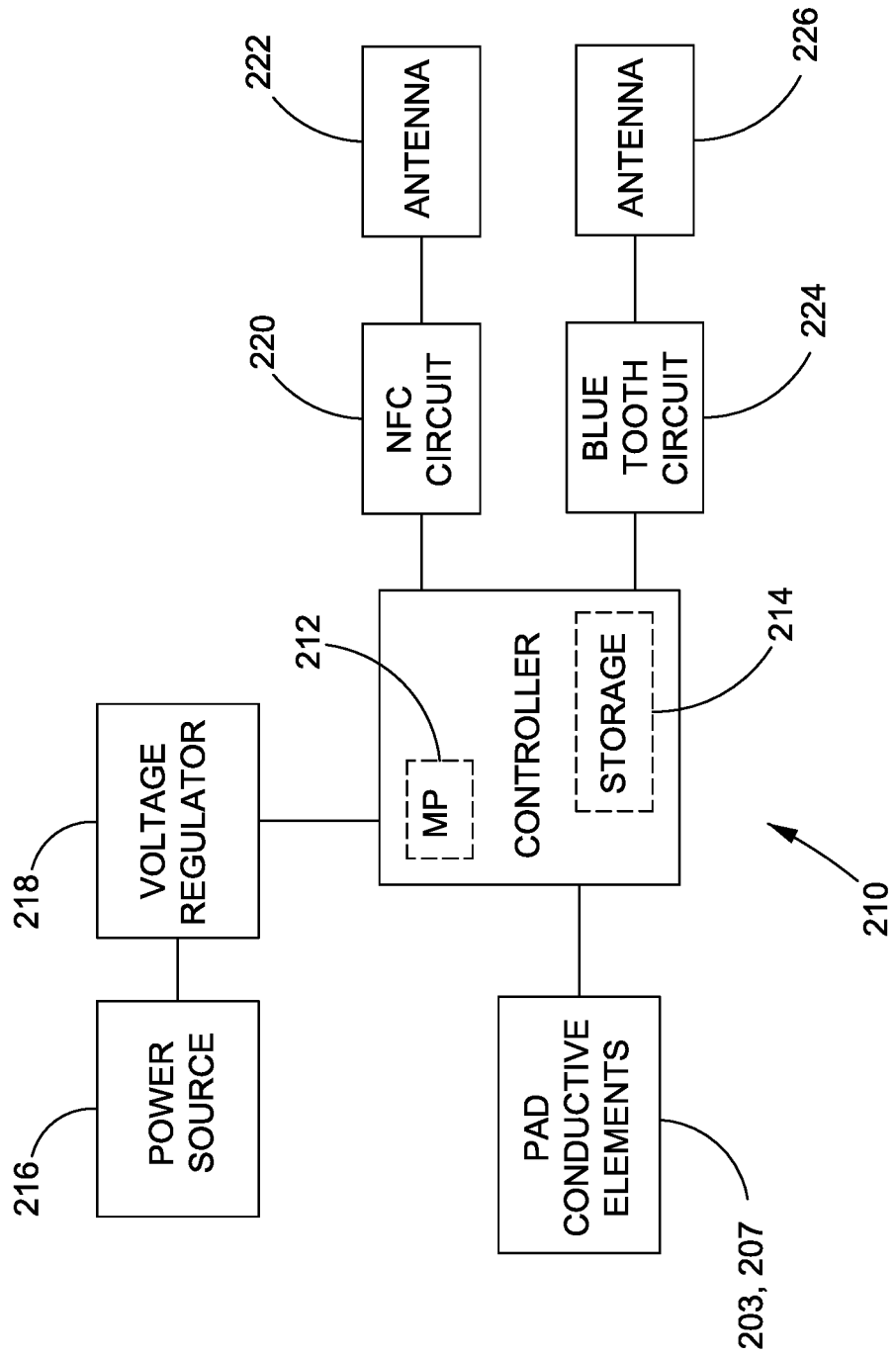
FIG. 11 illustrates block diagram of the sensor.
Figure 12:
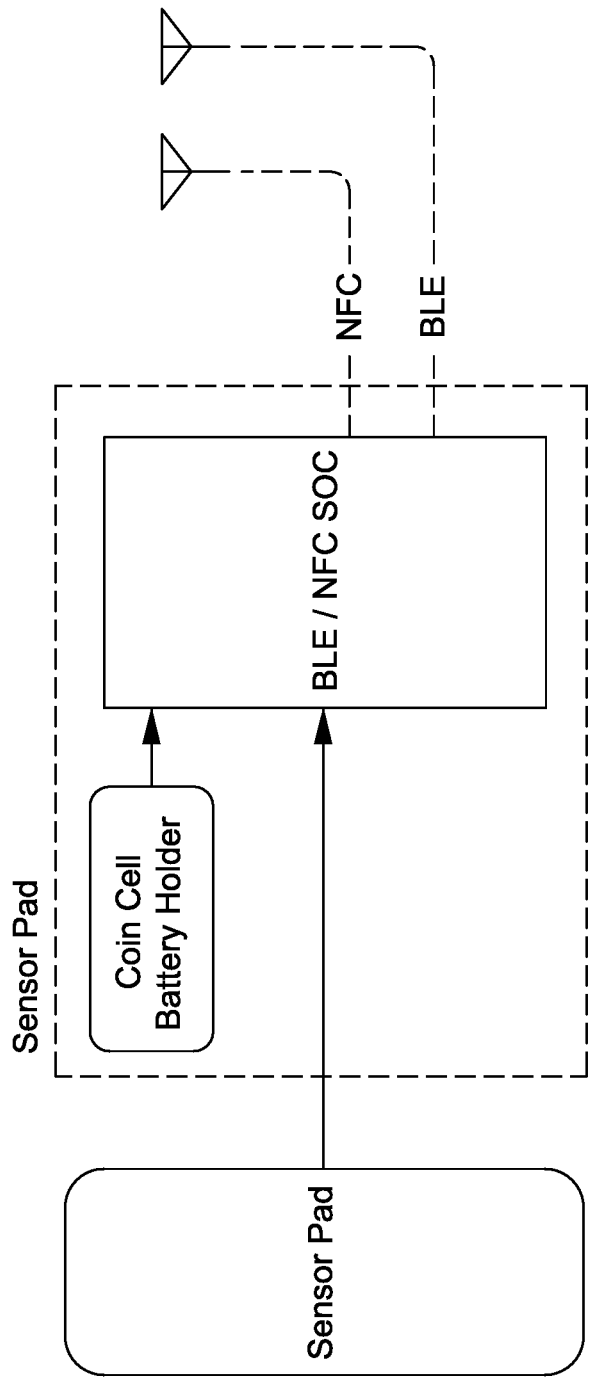
FIG. 12 illustrates a hardware architecture of the sensor.

FIG. 11 illustrates block diagram of the sensor 200 and FIG. 12 illustrates a hardware architecture of the sensor 200. Therein is shown a power source 216, a voltage regulator 218, an NFC circuit/module 220 having a connection with antenna 222, and a Bluetooth® circuit/module 224 having a connection with an antenna 226.

Figure 13:
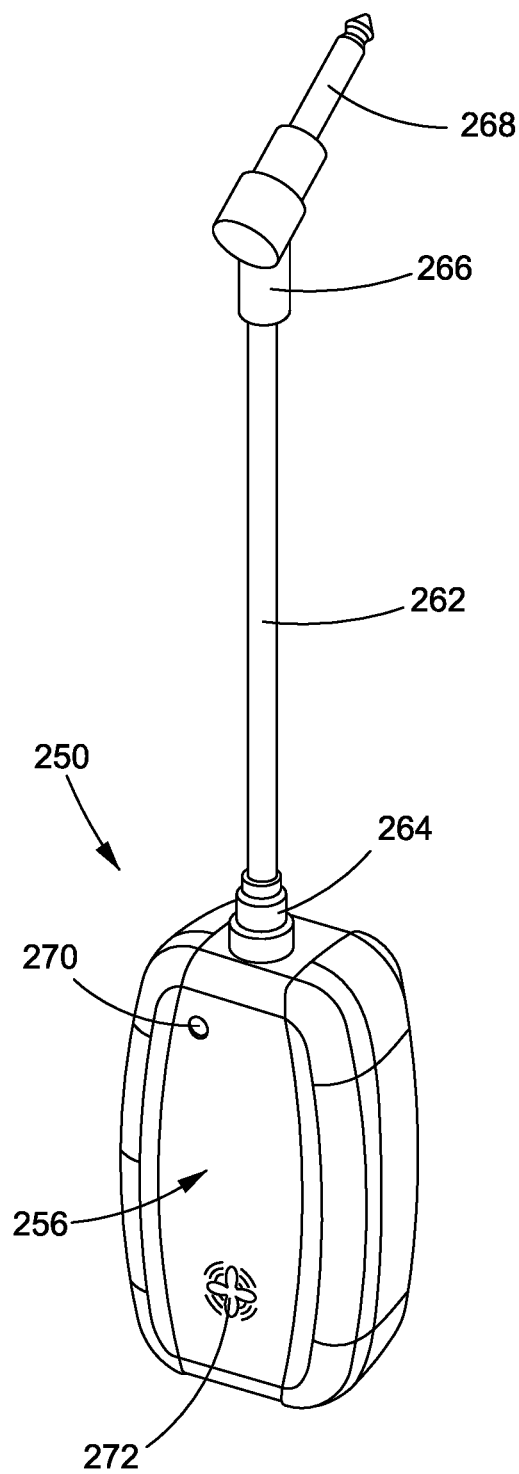
FIG. 13 illustrates a front perspective view of an adapter.

FIG. 13 illustrates a front perspective view of an adapter 250 with a housing 252, where a peripheral wall 254 defines a hollow interior 256. A proximal end 264 of the cable 262 is attached to the peripheral wall 254. A distal end 266 of the cable 262 is adapted with a plug 268. An adapter status indicator 270 is shown on the front of the adapter 250 but can be mounted in a different location. A pairing alignment mark 272 is also is shown on the front of the adapter 250 but can be mounted in a different location. The pairing alignment mark 272 is illustrated as a graphical item but can be provided as text.

Figure 14:
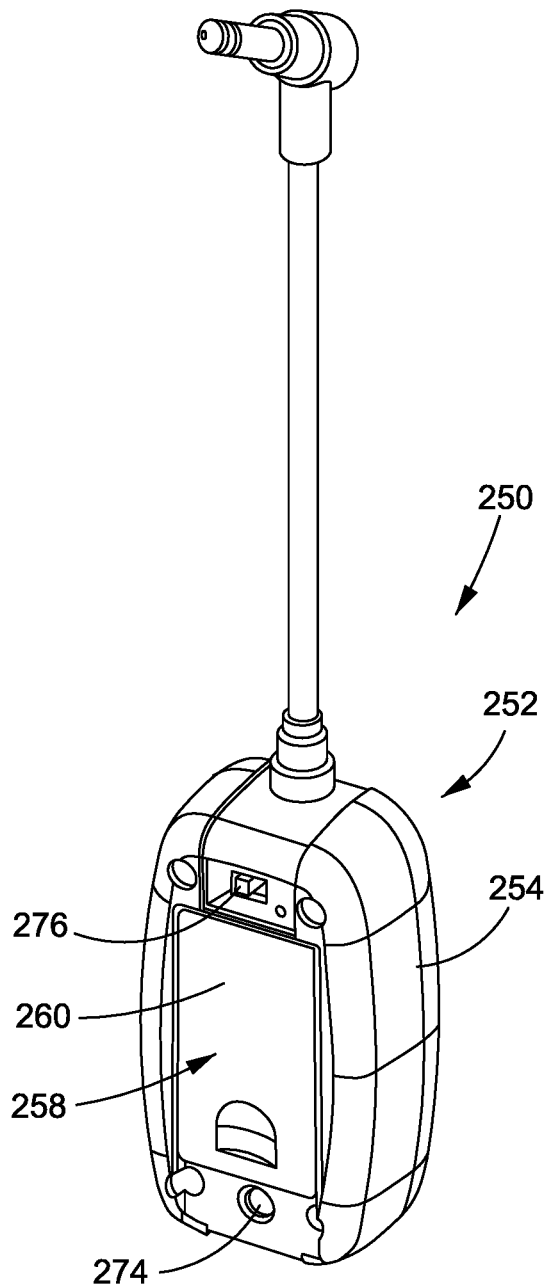
FIG. 14 illustrates a rear perspective view of the adapter.

FIG. 14 illustrates a rear perspective view of the adapter 250. A recess 258 is provided on the back of the peripheral wall 254 and houses a battery cover 260 below the power switch 276. Power source 274 is also shown, as a socket or port.

Figure 15:
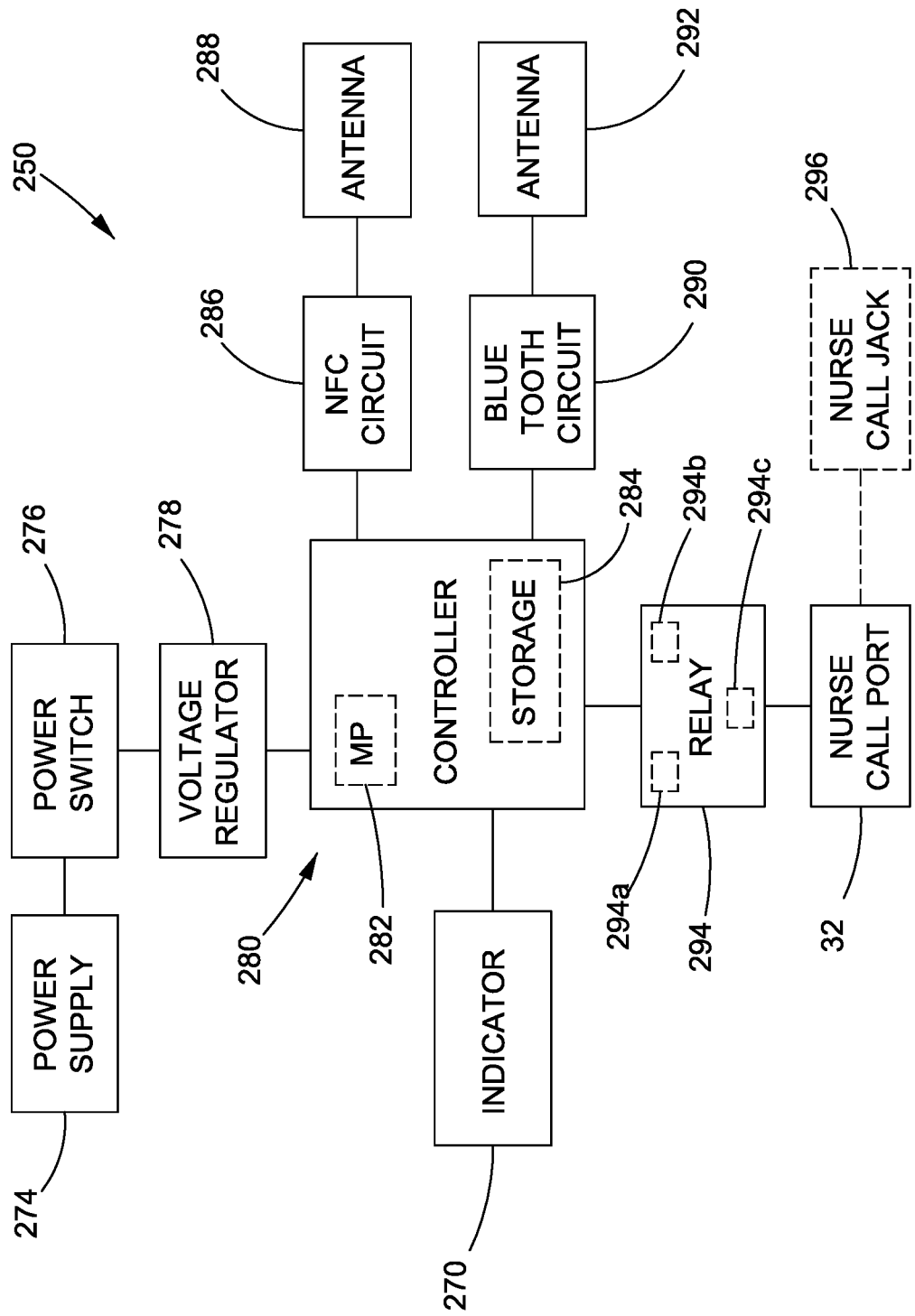
FIG. 15 illustrates a block diagram of the adapter.

FIG. 15 illustrates a block diagram of the adapter 250.

Figure 16:
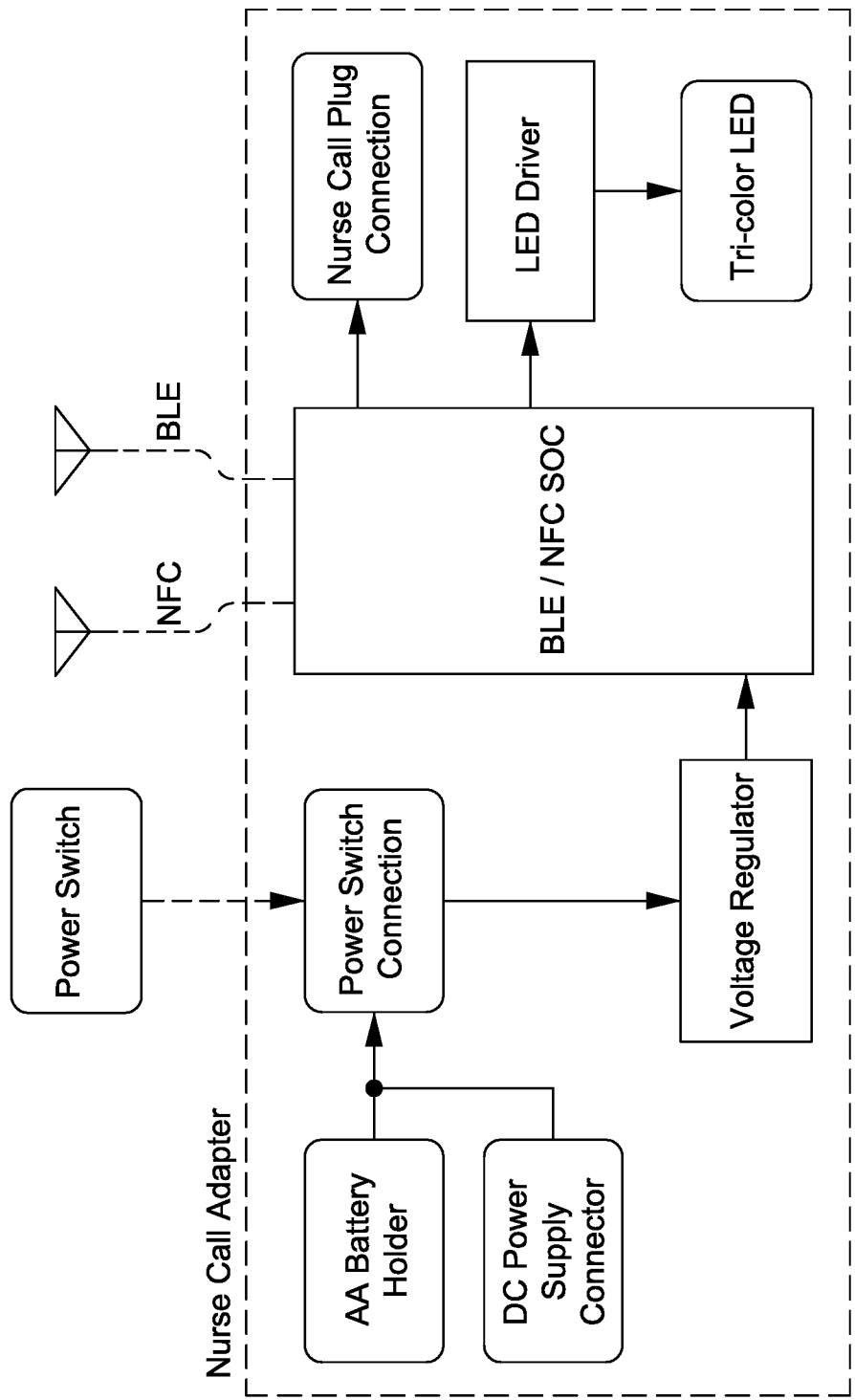
FIG. 16 illustrates a hardware architecture of the adapter.

FIG. 16 illustrates a hardware architecture of the adapter 250. Therein is shown a power source 274, a voltage regulator 278, an adapter controller 280 with a processor 282 and memory 284, an NFC circuit/module 286 having a connection with antenna 288, and a Bluetooth® circuit/module 290 having a connection with antenna 292. A relay 294 is electrically connected mediate the adapter controller 280 and the nurse call interface 32. The relay 294 comprises two coils 294a and 294b and a relay contact 294c. The nurse call port 32 is in a wired connection with the nurse call jack 296. Also related to FIG. 15, the nurse call adapter 250 can have, preferably, an automatic repairing feature. This can be timer based, or some other reasonable monitoring gap trigger. For example, a logic loop (not shown) can be employed that assesses if the adapter 250 is connected to monitor 12, and then provides visual and/or audio notification to confirm all is good or alert that action is needed by the caregiver.

What is claimed is:

1. A monitoring system, comprising:
    a sensor-adapter, the sensor-adapter comprising:
        a first pairing alignment mark; and
        a sensor-adapter controller, wherein the sensor-adapter controller includes a first wireless transceiver;
    a monitor, wherein the monitor comprises:
        a monitor controller disposed within a hollow interior housing;
        a second pairing alignment mark on an exterior of the housing; and
        a second wireless transceiver, wherein the second wireless transceiver is in wireless communication with the first wireless transceiver; wherein:
    the first wireless transceiver and the second wireless transceiver pair when the first pairing alignment mark and the second pairing alignment mark are positioned in proximity to one another; and
    the first wireless transceiver and the second wireless transceiver remain paired when the first pairing alignment mark and the second pairing alignment mark are moved out of proximity to one another.

2. The monitoring system of claim 1 wherein the monitor is designed to wirelessly pair with the sensor-adapter when only positioned by a user in a close proximity to the sensor-adapter or in direct contact with the sensor-adapter and without an additional action by the user nor a wired connection between the sensor-adapter and the monitor.

3. The monitoring system of claim 1, wherein the wireless connection comprises an RFID tag and RFID reader.

4. The monitoring system of claim 1, wherein the wireless connection comprises a wireless communication protocol.

5. The monitoring system of claim 1, wherein the wireless connection comprises a near field communication (NFC).

6. The monitoring system of claim 5, wherein NFC comprises an NFC tag in the sensor and an NFC reader in the monitor.

7. The monitoring system of claim 1, wherein the sensor-adapter controller is designed to wirelessly transmit, by the first wireless transceiver, a signal defining one of a sensing condition and a non-sensing condition.

8. The monitoring system of claim 7, wherein the signal is defining one of a physical pressure sensing condition and a physical non-pressure sensing condition.

9. The monitoring system of claim 7, wherein the signal transmitted by the first wireless transceiver is transmitted to the second wireless transceiver.

10. The monitoring system of claim 1, wherein the sensor-adapter is a pressure sensitive sensor.

11. The monitoring system of claim 10, wherein the pressure sensitive sensor is a pressure sensitive pad, and the pad comprises a body portion and a neck portion with a cover enclosing the pressure sensitive pad.

12. The monitoring system of claim 11, wherein the sensor controller is coupled to the pressure sensitive pad.

13. The monitoring system of claim 1, wherein the sensor-adapter is a nurse call adapter.

14. The monitoring system of claim 1, wherein the first wireless transceiver attempts to reconnect with the second wireless transceiver if the first wireless transceiver and the second wireless transceiver lose communication therebetween.

15. A monitoring system, comprising:
    a pressure sensitive sensor, the pressure sensitive sensor comprising:
        a first conductive layer;
        a second conductive layer, wherein the second conductive layer is selectively engageable with the first conductive layer;
        a non-conductive layer disposed between and separating the first conductive layer and the second conductive layer; and
        a cover enclosing the first conductive layer, the second conductive layer, and the non-conductive layer, wherein the cover defines a neck portion having an opening in an end portion;
    a sensor controller, wherein:
        the sensor controller is disposed within the neck portion of the cover;
        the sensor controller is coupled to at least one of the first conductive layer and the second conductive layer; and
        the sensor controller includes a first wireless transceiver; and
    a monitor, wherein the monitor comprises:
        a user interface;
        a monitor controller; and
        a second wireless transceiver.

16. The monitoring system of claim 15, wherein the first wireless transceiver and the second wireless transceiver are in wireless communication with one another such that the pressure sensitive sensor and the monitor are paired with one another.

17. The monitoring system of claim 15, wherein the sensor controller transmits, via the first wireless transceiver, a wireless signal defining one of a pressure sensing condition and a non-pressure sensing condition to the second wireless transceiver.

18. The monitoring system of claim 15, wherein the wireless signal transmits from the first wireless transceiver to the second wireless transceiver provided that the first wireless transceiver and the second wireless transceiver are within a communication range of one another.

19. The monitoring system of claim 15, wherein the first wireless transceiver attempts to reconnect with the second wireless transceiver if the first wireless transceiver and the second wireless transceiver lose communication therebetween.

20. The monitoring system of claim 15, wherein the monitor is designed to wirelessly pair with the sensor when only positioned by a user in a close proximity to the sensor or in direct contact with the sensor and without an additional action by the user nor a wired connection between the sensor and the monitor.

21. The monitoring system of claim 15, wherein the sensor comprises:
   a pressure sensitive pad with an electrical circuit and a neck portion, wherein the neck portion has an end with an opening; and
   a sensor controller disposed within the neck portion, wherein:
      the sensor controller is in wireless radio frequency (RF) communication with the monitor;
      the sensor controller wirelessly communicates to the monitor one of a pressure sensing condition and a non-pressure sensing condition after the sensor and the monitor are paired with each other in a wireless manner by aligning a pairing alignment mark on the monitor with a pairing alignment mark disposed adjacent to the first wireless transceiver in the sensor.

22. The monitoring system of claim 21, wherein the sensor is shaped and sized to maintain the opening.

23. The monitoring system of claim 15, wherein the sensor controller comprises:
   one or more processors; and
   a memory that is not a transitory propagating signal connected to the one or more processors and encoding computer readable instructions, including processor executable program instructions, accessible to the one or more processors, wherein the computer readable instructions, when executed by the one or more processors, cause the one or more processors to perform operations comprising:
      wirelessly pairing the sensor to the monitor;
      wirelessly transmitting a first electrical resistance value defining a deactivated condition when the first conductive layer is spaced apart from the second conductive layer by the middle layer; and
      wirelessly transmitting a second electrical resistance value defining an activated condition when the first conductive layer contacts the second conductive layer.

24. The monitoring system of claim 23, wherein the operations comprise wirelessly transmitting one of a sensor type, a unique sensor identifier, a battery status, and any combination thereof.

25. The monitoring system of claim 15, wherein the sensor controller is designed to receive a status request from the monitor and transmit a status response only in response to a receipt of the status request.

26. The monitoring system of claim 15, wherein the sensor controller is designed to wirelessly pair with a remote monitor in a first wireless mode and wirelessly communicate with the remote monitor in a second wireless mode.

27. The monitoring system of claim 26, wherein the first wireless mode comprises near field communication (NFC).

28. The monitoring system of claim 26, wherein the second wireless mode comprises short distance wireless communication.

29. The monitoring system of claim 7, further comprising a plurality of sensor-adapters and wherein the signal is defining at least one of the plurality of sensor-adapters has a condition from the group comprising (i) a low battery and (ii) a lost communication signal.

30. The monitoring system of claim 29, wherein the monitor receives the signal and then provides a notification to the caregiver.

31. The monitoring system of claim 30, wherein the notification is specific to the condition of the low battery or the lost communication signal.

* * * * *